(12) United States Patent
Mann et al.

(10) Patent No.: US 10,894,041 B2
(45) Date of Patent: *Jan. 19, 2021

(54) MEDICAL TREATMENTS BASED ON ANAMORELIN

(71) Applicant: HELSINN HEALTHCARE SA, Lugano/Pazzallo (CH)

(72) Inventors: William Mann, Hoboken, NJ (US); John Friend, Colts Neck, NJ (US); William Polvino, Tinton Falls, NJ (US); Suzan Allen, Georgetown, TX (US); Ming Lu, Plainsboro, NJ (US); Elizabeth Duus, Cape Coral, FL (US); Ruben Giorgino, Allschwil (CH); Enrico Baroni, Cernobbio (IT)

(73) Assignee: Helsinn Healthcare SA, Lugano/Pazzallo (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/275,669

(22) Filed: Feb. 14, 2019

(65) Prior Publication Data
US 2019/0175574 A1    Jun. 13, 2019

Related U.S. Application Data

(63) Continuation of application No. 15/590,025, filed on May 9, 2017, now Pat. No. 10,278,964, which is a continuation of application No. 14/839,038, filed on Aug. 28, 2015, now Pat. No. 9,675,600.

(60) Provisional application No. 62/045,976, filed on Sep. 4, 2014.

(51) Int. Cl.
*A61K 31/454*    (2006.01)
*A61K 31/00*    (2006.01)

(52) U.S. Cl.
CPC ............ *A61K 31/454* (2013.01); *A61K 31/00* (2013.01)

(58) Field of Classification Search
CPC .............................. A61K 31/454; A61K 31/00
See application file for complete search history.

(56) References Cited

U.S. PATENT DOCUMENTS

| | | | |
|---|---|---|---|
| 6,303,620 B1 | 10/2001 | Hansen et al. |
| 7,994,329 B2 | 8/2011 | Ankerson |
| 8,288,427 B2 | 10/2012 | Mann et al. |
| 8,394,833 B2 | 3/2013 | Mann et al. |
| 2005/0261201 A1 | 11/2005 | Polvino et al. |
| 2007/0004638 A1 | 1/2007 | Lorimer et al. |
| 2008/0207640 A1 | 8/2008 | Polvino |

FOREIGN PATENT DOCUMENTS

| | | |
|---|---|---|
| WO | 2005/014032 A2 | 2/2005 |
| WO | 2008/124183 A1 | 10/2008 |
| WO | 2013/158874 A1 | 10/2013 |
| WO | 2013/175805 A1 | 11/2013 |

OTHER PUBLICATIONS

Currow, David et al., The Effect of Anamorelin on Body Composition of Patients With Advanced Non-Small Cell Lung Cancer (NSCLC) and Anorexia/Cachexia: Pooled Analysis of Two Phase 3 Trials; MASCC/ISOO Jun. 21-23, 2019, Abstract MASCC9-0624; San Francisco, CA; 1 pp.
Lesniak et al., Effects of megestrol acetate in patients with cancer anorexia-cachexia syndrome—a systematic review and meta-analysis_ Pol Arch Med Wewn. Nov. 2008; 118(11):636-44.
Del Fabbro et al. Effects of melatonin on appetite and other symptoms in patients with advanced cancer and cachexia: a double-blind placebo-controlled trial. J. Clin. Oncol. Apr. 1, 2013 ;31(10):1271-1276.
Dobs AS et al., Effects of enobosarm on muscle wasting and physical function in patients with cancer: a doubleblind, randomised controlled phase 2 trial. Dobs AS et al., www_thelancetcom/oncology Published online Mar. 14, 2013 http://dx.doi.org/10.1016/S 1470-2045(13)70055-X.
Garcia, J.M., Polvino, W.J. Effect on body weight and safety of RC-1291, a novel, orally available ghrelin mimetic and growth hormone secretagogue: results of a phase I, randomized, placebo-controlled, multiple-dose study in healthy volunteers, Oncologist, 2007;12:594-600.
Garcia, J.M., Polvino, W.J. Pharmacodynamic hormonal effects of anamorelin, a novel oral ghrelin mimetic and growth hormone secretagogue in healthy volunteers, Growth Horm IGF Res, 2009;19:267-73.
Garcia, et al. Therapeutic potential of anamorelin, a novel, oral ghrelin mimetic, in patients with cancer-related cachexia: a multi-center, randomized, double-blind, crossover, pilot study, Support Care Cancer, 2013; 21:129-37.
Garcia, et al. A phase II randomized, placebo-controlled, double-blind study of the efficacy and safety of RC-1291 (RC) for the treatment of cancer cachexia, J Clin Oneal, 2007;25:18(S):9133.
Temel J.B., S; Jain, Met al. Efficacy and safety of anamorelin HCI in NSCLC patients: results from a randomized, double-blind, placebo-controlled, multicenter phase II study, Presented at the European Cancer Congress, Sep. 27-Oct. 1, 2013, Amsterdam, Netherlands; Abstract No. 1308.
Uchuno, et al. Presentation entitled: ON0-7643/anamorelin for the treatment of patients with non-small cell lung cancer and cachexia: results from phase 2 study with Japanese patients; ESMO Congress, 2016.
The Functional Assessment of Chronic Illness Therapy (FACIT) Measurement System: properties, applications, and interpretation by Webster, K, Cella, D, and Yost, K, Health and Quality of Life Outcomes, vol. 1, published 2003.
Manir, Indian J Palliat Care. May-Aug. 2012; 18(2): 109-116.
Temel, et al. Evaluation of quality of life from a phase II study of anamorelin HCI in NSCLC patients; J Clin Oncol 31, 2013 (suppl 31; abstr 42).

(Continued)

*Primary Examiner* — Sahar Javanmard
(74) *Attorney, Agent, or Firm* — Clark G. Sullivan

(57) ABSTRACT

Methods of treating cancer related conditions using anamorelin are described.

17 Claims, 15 Drawing Sheets

(56) References Cited

OTHER PUBLICATIONS

Tellen SB, Cella Of, Webster K, Blendowski C, Kaplan E. Measuring fatigue and other anemia-related symptoms with the Functional Assessment of Cancer Therapy (FACT) measurement system. J Pain Symptom Manage. 1997;13:63-74. [PubMed: 9095563].

Cella DF, Bonomi AE, Leslie WT, Von Roenn J, Tchekmeydian NS. Quality of life and nutritional wellbeing, Measurements and relationship. Oncology. 1993;79(suppl): 105-11.

Minton O, Stone P.A. systematic review of the scales used for the measurement of cancer-related fatigue (CRF) Ann Oncol. 2009;20:17-25. [PubMed: 18678767].

FAACT refers to Functional Assessment of Anorexia Cachexia Therapy (FAACT) Questionnaire: Quality of Life and Nutrition in the Patient with Cancer by Small, W, Carrara, R, Danford, L, Logemann, J, and Cella, D, ACCC's Integrating Nutrition Into Your Cancer Program, pp. 13-14, published Mar./Apr. 2002.

Temel, et al. Anamorelin in patients with non-small-cell lung cancer and cachexia (ROMANA 1 and ROMANA 2): results from two randomised, double-blind, phase 3 trials; The Lancet: Oncology vol. 17 (Apr. 2016) pp. 519-531.

Oken, M.M., Creech, RH, Tormey, D.C., Horton, J., Davis, T.E., McFadden, E.T., Carbone, P.P.: Toxicity and Response Criteria of the Eastern Cooperative Oncology Group. Am J Clin Oncol 5:649-555, 1982.

Abernethy, et al. Anamorelin for the treatment of cancer anorexia-cachexia: Baseline characteristics from three phase III clinical trials (the ROMANA program); J. Clin. Oncology, 2014 ASCO Annual Meeting Abstracts. vol. 32, No. 15_suppl (May 20 Supplement), 2014:e20694.

Currow, et al. Anamorelin in cachectic patients with non-small cell lung cancer (NSCLC) and low BMI (< 20 kg/m2): A pooled efficacy data analysis of two phase 3 studies; J Clin Oneal 34, 2016 (suppl; abstr 10119).

Garcia, et al. Anamorelin for patients with cancer cachexia: an integrated analysis of two phase 2, randomised, placebo-controlled, doubleblind trials; Lancet Oncol. Jan. 2015;16(1):108-16.

Salsman, et al. Brief versions of the FACIT-fatigue and FAACT subscales for patients with non-small cell lung cancer cachexia; Support Care Cancer (2015) 23:1355-1364.

Sanger et al. Ghrelin and motilin receptors as drug targets for gastrointestinal disorders; Nature Reviews: Gastroenterology & Hepatology; vol. 13 (2016) pp. 38-48.

Lok, Corie. The Last Illness: Researchers are gaining insight into the causes of Cachexia—a devastating form of muscle wasting that is often the final stage of cancer and other diseases; pp. 182-183, Nature, vol. 528:Dec. 10, 2015.

Temel, et al. (Abstract) Efficacy and safety of anamorelin HCI in NSCLC patients: Results from a randomized, double-blind, placebo-controlled, multicenter phase II study; SCWD, Kobe Dec. 9-11, 2013.

Pharmacokinetic (PK) Profile of RC-1291, a novel Oral Ghrelin mimetic for the treatment of Cancer Anorexia/cachexia 26 R. —Blum, W. Polvino (Poster) Support Care Cancer (2006) 14: 583-687 DOI 10.1007/s00520-006-0078-x (abstract 03-010).

Evaluation of quality of life from a Phase II study of anamorelin HCI in NSCLC patients; J. Temel, S. Bondarde, M. Jain, S. Allen, W. Mann (Poster) ASCO-QCS 2013.

Evaluation of Anorexia-Cachexia Symptoms/Concerns from ROMANA 2, a Phase III Trial of Anamorelin in Non-Small Cell Lung Cancer Patients with Cachexia C_ Brewer, A. Abernethy, O. Currow, K. Fearon, J. Friend, J. Temel Poster) Oncology Nursing Forum 2015; 42, E229 [Poster #71].

Gelhom, et al. Psychometric Properties of the FAACT Additional Concerns Subscale (A/CS) for Measurement of Anorexia in Patients with Non-Small Cell Lung Cancer; Evidera 1005; ISOQOL 23rd Annual Conference; Oct. 19-22, 2016; Copenhagen, Denmark.

Kumor, et al.; Biologic activity of RC-1291, a novel oral ghrelin mimetic for the treatment of cancer anorexia/cachexia: Results from phase I randomized, double-blind, placebo-controlled clinical trial in healthy volunteers; (Poster) Sapphine Therapeutics 2006.

Garcia et al. Cancer & Metabolism 2014, 2(Suppl 1):P19.

Sumbul, et al. Curr Opin Support Palliat Care. Dec. 2013; 7(4): 368-375.

Partial Supplemental EP Search Report issued in corresponding EP application No. 15838548.4 dated Jun. 6, 2017.

132 Declaration of Ruben Giorgio, MD, Ph.D, from U.S. Appl. No. 14/839,038, filed Nov. 8, 2016.

International Search Report and Written Opinion issued in corresponding International Application No. PCT/US15/47435 dated Dec. 14, 2015.

TBM=total body mass; LBM=lean body mass; FM=fat mass; BM=bone mass

MEDICAL TREATMENTS BASED ON ANAMORELIN

FIELD OF THE INVENTION

This invention relates to pharmaceutical treatments using anamorelin, and relates particularly to the treatment of conditions and disorders associated with cancer cachexia.

BACKGROUND

Cancer cachexia, often referred to as cancer anorexia-cachexia syndrome (CACS), is a multifactorial condition with a high prevalence in non-small cell lung cancer (NSCLC). Cancer cachexia is characterized by decreased body weight (mainly lean body mass; LBM), and is associated with worsened morbidity and survival. Standard effective treatments are lacking, although anamorelin has shown promise as a treatment in this field. Anamorelin is a novel, selective ghrelin receptor agonist with appetite-enhancing and anabolic activity.

A standard off-label therapy for cancer cachexia is megestrol acetate, which is approved to increase appetite and prevent weight loss in patients with AIDS. However, megestrol has only been shown to increase body weight and water in patients, and does not improve fat mass or lean body mass.

Megestrol acetate also has not been shown to improve quality of life in cancer cachexia patients. Lesniak et al. conducted a systematic review of clinical trials with megestrol acetate, and reported: "Based on a systematic review of trials with megesterol acetate in patients with cancer anorexia-cachexia syndrome, quality of life was measured using different scales in 14 studies, and in 13 of the 14 studies, there was no significant difference between patients receiving megesterol acetate and those taking placebo, dronabinol, eicosapentaenoic acid or glucocorticosteroids." Leśniak Wl, Bała M, Jaeschke R, Krzakowski M., Effects of megestrol acetate in patients with cancer anorexia-cachexia syndrome—a systematic review and meta-analysis. Pol Arch Med Wewn. 2008 November; 118(11):636-44.

Other drugs have also failed to improve the quality of life in cancer cachexia patients. Del Fabbro reported a double-blind placebo-controlled trial and the effect of melatonin on appetite and other symptoms in patients with advanced cancer and cachexia. No differences between melatonin and placebo groups after 4 weeks were observed regarding weight, body composition (including fat-free mass), symptom scores, and quality-of-life outcomes (as measured by FACIT-F and FAACT). Del Fabbro E1, Dev R, Hui D, Palmer L, Bruera E. Effects of melatonin on appetite and other symptoms in patients with advanced cancer and cachexia: a double-blind placebo-controlled trial. J Clin Oncol. 2013 Apr. 1; 31(10):1271-6.

Enobosarm ((2S)-3-(4-cyanophenoxy)-N-[4-cyano-3-(trifluoromethyl)phenyl]-2-hydroxy-2-methylpropanamide) (also known as Ostarine, GTx-024 and MK-2866) is an investigational selective androgen receptor modulator (SARM) under development for conditions such as muscle wasting and osteoporosis. Dobs et al. report phase 2 data that includes some quality of life data as measured by FAACT/FACIT-F, but it only compares the measurements to baseline within treatment arms rather than assessing active versus placebo, rendering any conclusions difficult to reach. Dobs A S et al., Effects of enobosarm on muscle wasting and physical function in patients with cancer: a double-blind, randomised controlled phase 2 trial. Dobs A S et al., www.thelancet.com/oncology Published online Mar. 14, 2013 http://dx.doi.org/10.1016/S1470-2045(13)70055-X.

Garcia and Polvino performed a Phase I study (single-center, randomized, double-blind, and placebo-controlled) in which healthy subjects were divided into three dosage groups. Garcia, J. M., Polvino, W. J. Effect on body weight and safety of RC-1291, a novel, orally available ghrelin mimetic and growth hormone secretagogue: results of a phase I, randomized, placebo-controlled, multiple-dose study in healthy volunteers, Oncologist, 2007; 12:594-500. The first group received placebo or 25 mg anamorelin once per day, for 5 days. The second group received anamorelin at either 25 mg twice per day or 50 mg once per day for 6 days, and then crossed over to the other dosage regimen for 5 days; three subjects in this group received placebo for all 11 doses to maintain double-blinding. The third group received placebo or 75 mg anamorelin once per day for 6 days. Subjects who received anamorelin at either 50 or 75 mg doses had significant dose-related weight gain after 6 days versus placebo, with the greatest increases seen with daily dosing. The mean increase in body weight from baseline after 50 mg (once daily dose or split-dose regimen) or 75 mg anamorelin once per day was significant relative to placebo.

A follow-up study by Garcia and Polvino characterized the effects of anamorelin on growth hormone (GH) levels in healthy subjects, as well as its effects on insulin-like growth factor 1 (IGF-1), insulin-like growth factor binding protein 3 (IGFBP-3), serum hormone profiles, and carbohydrate metabolism. Garcia, J. M., Polvino, W. J. Pharmacodynamic hormonal effects of anamorelin, a novel oral ghrelin mimetic and growth hormone secretagogue in healthy volunteers, Growth Horm IGF Res, 2009; 19:267-73. This study (single-center, randomized, double-blind, and placebo-controlled) used the same dosage groups as the previous study (i.e., one group received placebo or a single dose of 25 mg anamorelin once per day, the second group received placebo or either 25 mg anamorelin twice per day or 50 mg anamorelin once per day for 6 days, and then switched to the other dosage regimen for 5 days, and the third group received placebo or 75 mg anamorelin once per day). All doses of anamorelin significantly increased GH and IGF-1 levels, particularly the 50 mg single dose and 75 mg dose; the split 50 mg dose showed an increase in GH and IGF-1 levels, but not to the same degree as the single 50 mg dose. Again, significant increases in body weight were seen in groups receiving the 50 mg dose (single or split dose) and 75 mg dose. Increases in body weight correlated strongly with increases in IGF-1 levels.

Garcia et al then performed a pilot study (multicenter, randomized, double-blind, placebo-controlled, crossover study) of anamorelin treatment in patients with various cancers and cachexia who had an involuntary body weight loss of over 5% in the previous 6 months, an estimated life expectancy of over 3 months, and an Eastern Cooperative Oncology Group (ECOG) performance status of 0-2. Garcia, J. M., Friend, J., Allen, S. Therapeutic potential of anamorelin, a novel, oral ghrelin mimetic, in patients with cancer-related cachexia: a multicenter, randomized, double-blind, crossover, pilot study, Support Care Cancer, 2013; 21:129-37. A single dose of 50 mg anamorelin or placebo was given once per day over the course of the study, followed by a 3 to 7-day washout period, and then treatments were switched. Study assessments included body weight, appetite, food intake, growth hormone (GH) levels, and patient-reported symptom assessment (as measured by the Anderson Symptom Assessment Scale (ASAS), the Functional Assessment of Chronic Illness Therapy With Additional Fatigue Domain (FACIT-F), and the Bristol-Myers Anorexia/Cachexia Recovery Instrument, 7-question version (BACRI-7)). Anamorelin significantly increased body weight compared with placebo. GH, IGF-1, and IGFBP-3 levels also significantly increased with anamorelin, particularly in terms of the mean serum concentrations of the hormones. Food intake increased but not significantly. Patient-reported appetite significantly improved with anamorelin as measured by ASAS; as measured by BACRI-7, there was no significant difference in appetite among treatment groups although significantly more patients reported greater enjoyment from eating while on anamorelin therapy. Anamorelin treatment also significantly increased FACIT-F scores.

Garcia et al performed a phase II trial (multicenter, randomized, double-blind, and placebo-controlled) lasting 12 weeks and including 81 patients with various cancers with cachexia (body weight loss of over 5% within the previous 6 months), and an ECOG score of 0-2. Garcia, J., Boccia, R. V., Graham, C., Kumor, K., Polvino, W. A phase II randomized, placebo-controlled, double-blind study of the efficacy and safety of RC-1291 (RC) for the treatment of cancer cachexia, J Clin Oncol, 2007; 25:18(S):9133. Patients received either 50 mg anamorelin once per day or placebo during the 12-week study, and quality of life (FACIT-F), weight gain, IGF-1 and IGFBP-3 were measured over the course of the trial. Total and lean body mass significantly increased as compared to placebo at weeks 4 and 8; the magnitude of the increase was stable from weeks 4 to 12 for both total and lean body mass. Fat mass decreased more in placebo-treated patients than in anamorelin-treated patients, although the difference did not reach statistical significance. See WO/2008/124183 of Mann and Polvino. Interestingly, no corresponding increase in scale weight measures was noted. Levels of IGF-1 and IGFBP-3 were significantly increased at weeks 4, 8, and 12. No significant effects on quality of life as measured by the FACIT-F test were noted. However, ASAS scores were improved. See WO/2008/124183 of Mann and Polvino.

Temel et al conducted a phase II study (multicenter, randomized, double-blind, and placebo-controlled) lasting 12 weeks in 226 patients with advanced non-small cell lung cancer (NSCLC) and an ECOG score 0-1 who were candidates for treatment with carboplatin/paclitaxel (with or without bevacizumab). Temel J. B., S; Jain, M et al. Efficacy and safety of anamorelin HCl in NSCLC patients: results from a randomized, double-blind, placebo-controlled, multicenter phase II study, Presented at the European Cancer Congress, 27 Sep.-1 Oct. 2013, Amsterdam, Netherlands; Abstract no 1308. Patients were given once daily doses of 50 or 100 mg anamorelin or matching placebo, and weight gain and IGFBP-3 levels were measured over the course of the study. The group receiving 100 mg anamorelin had a statistically significant average weight gain from baseline to week 12. Anamorelin therapy led to statistically significant increases in IGFBP-3 as compared to placebo. Anamorelin also improved patient scores on the MD Anderson Symptom Inventory (MDASI), which measures the severity of symptoms on daily functioning among cancer patients, although the improvement was not significant.

A Study of anamorelin in NSCLC, presented at ASCO Quality Care 2013, included results of individual MDASI questions, including the response on fatigue. This study was only in NSCLC patients, not in NSCLC patients suffering from cachexia. http://meetinglibrary.asco.org/content/119980-140

U.S. Pat. No. 6,303,620 discloses the use of novel compounds including anamorelin for: reducing cachexia due to cancer; treating anorexia; regulating food intake; improving muscle strength; treating chronic or acute fatigue syndrome and insulin resistance; treating conditions which require increased plasma GH levels; treating immunosuppressed patients; and treating cardiomyopathy, cardiac failure, impaired cardiac function, and myocardial infarction.

U.S. Pat. No. 7,994,329 discloses the use of agonists of growth hormone secretagogue receptor type 1A (GHSR 1A) for use in medicaments for the regulation of food intake, body mass index (BMI), and the treatment of anorexia, type II diabetes and wasting associated with various diseases and conditions.

U.S. Pat. No. 8,394,833 discloses the use of anamorelin for reducing nausea, treating emesis and also evaluated quality of life as measured by the ASAS (rating of the severity from 1-10 of the following symptoms: pain, fatigue, nausea, depression, anxiety, drowsiness, shortness of breath, appetite, sleep and feeling of well-being) and the use of growth hormone secretagogues for increasing appetite and body weight and IGF-1 levels.

U.S. Pub. No. 2005/0261201 discloses the use of a growth hormone secretagogue for reducing C-reactive protein in a patient suffering from cachexia, anorexia, chronic fatigue syndrome, diabetes, and tumor metastasis as well as inducing secretion of GH and IGF-1, and its use in treating a patient who has had or who is at risk of a vascular event such as myocardial infarction.

WO/2013/158874 discloses the use of anamorelin HCl for the treatment of cancer-related cachexia and conditions which require increased plasma GH levels, and the use of growth hormone secretagogues for increasing appetite and body weight.

None of these patent publications discloses the use of anamorelin to treat early satiety or fatigue resulting from cachexia, or for increasing survival time of terminally ill cancer patients. They also do not disclose improvement of patient quality of life as measured by the anorexia/cachexia domain of the Functional Assessment of Anorexia/Cachexia Therapy (FAACT) assessment, which measures physical and functional well-being as well as specific concerns related to anorexia and cachexia by asking questions directed to body weight/image, appetite, food consumption, vomiting, early satiety, and stomach pain.

SUMMARY OF THE INVENTION

The inventors have developed several methods for treating disorders and conditions associated with cancer cachexia using anamorelin. A first principal embodiment relates to the unique condition of patients defining this condition, and the surprising ability of anamorelin to increase lean body mass in this population. In this embodiment the invention provides a method of treating cachexia in a human cancer patient, comprising administering to said patient a therapeutically effective amount of anamorelin for a therapeutically effective period of time.

In another embodiment the invention provides a method of treating cachexia in certain well-defined patient groups, such as a human cancer patient suffering from unresectable Stage III or IV non-small cell lung cancer and cachexia as defined by body weight loss greater than or equal to 5% in the previous 6 months or body mass index less than 20 kg/m$^2$, by increasing the lean body mass of said patient, comprising administering to said patient a therapeutically effective amount of anamorelin for a therapeutically effective period of time.

Another embodiment relates to the unexpected ability of anamorelin to defeat the early satiety that commonly occurs in cancer cachexia and other related conditions. In this embodiment the invention provides a method of treating early satiety resulting from cancer cachexia in a human cancer patient comprising administering to said patient a therapeutically effective amount of anamorelin for a therapeutically effective period of time.

A fourth principal embodiment relates to the unexpected ability of anamorelin to treat the fatigue that is often associated with cancer and cancer treatments. In this embodiment the invention provides a method of treating fatigue resulting from cancer cachexia in a human cancer patient comprising administering to said patient a therapeutically effective amount of anamorelin for a therapeutically effective period of time.

A fifth principal embodiment relates to the use of anamorelin to increase the survival time of cancer patients. In this embodiment the invention provides a method of increasing the survival time of a terminally ill cancer patient comprising administering to said patient a therapeutically effective amount of anamorelin for a therapeutically effective period of time.

A sixth principal embodiment relates to the use of anamorelin to improve specific quality of life measures in cancer cachexia patients. In this embodiment the invention provides a method of improving quality of life as measured by FAACT in the anorexia/cachexia domain in a human cancer patient comprising administering to said patient a therapeutically effective amount of anamorelin for a therapeutically effective period of time.

A seventh principal embodiment relates to the use of anamorelin to improve different measures of body mass. In this embodiment the invention provides a method of increasing total body mass, lean body mass, and fat mass in a human patient suffering from cancer cachexia comprising administering to said patient a therapeutically effective amount of anamorelin for a therapeutically effective period of time. The increase in fat mass is particularly beneficial because it reflects an increase in stored energy in these frequently weak and malnourished patients.

An eighth principal embodiment relates to the use of anamorelin to improve other quality of life measures in cancer cachexia patients. In this embodiment, the invention provides a method of improving quality of life in a human cancer patient comprising administering to said patient a therapeutically effective amount of anamorelin for a therapeutically effective period of time, wherein the quality of life improvement is measured by:
 FAACT (Total Score or TOI);
 SEA Score;
 SEF Score;
 FACIT-G (Total Score or TOI); or
 FACIT-F (Total Score or TOI).

In any of the foregoing principal embodiments, the administration is preferably oral. In addition, the administration is preferably done on a once-daily basis. Additional advantages of the invention are set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Definition and Use of Terms

Figure 1:
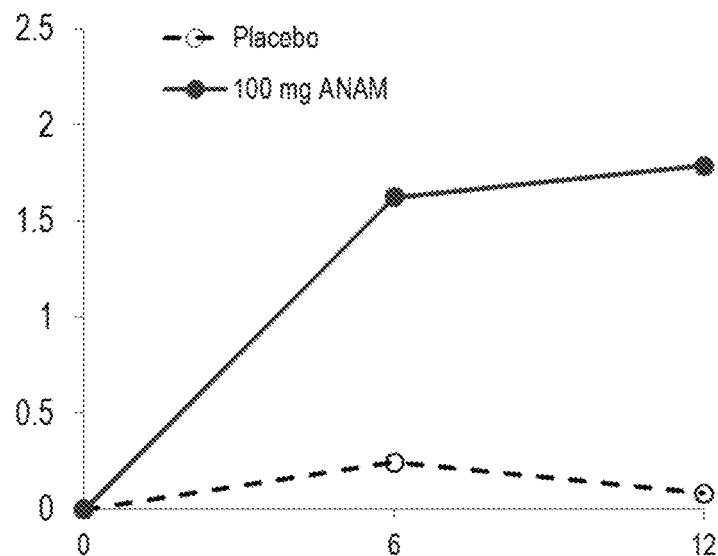
FIG. 1 is a graphical representation of the primary efficacy outcome (lean body mass) in terms of the median change from baseline in the intent to treat ("ITT") population, for patients receiving anamorelin and placebo (PBO) in Romana 1. Data shown are observed values only (i.e., no modeling or imputation for missing data).

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

When the singular forms "a," "an" and "the" or like terms are used herein, they will be understood to include plural referents unless the context clearly dictates otherwise. Thus, for example, reference to "a hydrocarbon" includes mixtures of two or more such hydrocarbons, and the like. The word "or" or like terms as used herein means any one member of a particular list and also includes any combination of members of that list.

When used herein the term "about" or "ca." will compensate for variability allowed for in the pharmaceutical industry and inherent in pharmaceutical products, such as differences in product strength and bioavailability due to manufacturing variations and time-induced product degradation. The term allows for any variation which in the practice of pharmaceuticals would allow the product being evaluated to be considered pharmaceutically equivalent or bioequivalent, or both if the context requires, to the recited strength of a claimed product. It will be understood that all numeric values expressed in this document can be prefaced by the term "about."

Throughout the description and claims of this specification, the word "comprise" and variations of the word, such as "comprising" and "comprises," means "including but not limited to," and is not intended to exclude, for example, other additives, components, integers or steps.

When a range of values can be used to describe a particular regimen, it will be understood that the range can be defined by selectively combining any one of the lower end of variables described in the specification with any one of the upper end of variables described in the specification that is mathematically possible.

Throughout this application, whenever a standard is given with reference to a test or methodology currently accepted and applied in the scientific community, the standard will be understood to be evaluated with respect to the test or methodology as it is reported in the published literature on Jul. 1, 2014.

The terms "treating" and "treatment," when used herein, refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "significantly" refers to a level of statistical significance. The level of statistical significant can be, for example, of at least $p<0.05$, of at least $p<0.01$, of at least $p<0.005$, or of at least $p<0.001$. Unless otherwise specified, the level of statistical significance when recited is $p<0.05$. When a measurable result or effect is expressed or identified herein, it will be understood that the result or effect is preferably evaluated based upon its statistical significance relative to a baseline. In like manner, when a treatment is described herein, it will be understood that the treatment preferably shows efficacy to a degree of statistical significance.

As used herein, "therapeutically effective amount" refers to an amount sufficient to elicit the desired biological response. The therapeutically effective amount or dose will depend on the age, sex and weight of the patient, and the current medical condition of the patient. The skilled artisan will be able to determine appropriate dosages depending on these and other factors in addition to the present disclosure.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. "Pharmaceutically acceptable salts" means salts that are pharmaceutically acceptable, as defined above, and which possess the desired pharmacological activity.

When a weight of an active ingredient is given without reference to the free base or salt of the active ingredient, it will be understood that the weight can refer to the weight of the free base of the weight or the entire salt.

"Cachexia" can be defined by a variety of methods in any of the principal embodiments or subembodiments of the present invention. In particular, and of the following definitions can be used:

a clinical syndrome characterised by one or a combination of anorexia, early satiety, weight loss, muscle wasting, anemia, and oedema, but is preferably defined by 3, 4, 5 or all of these conditions.

body weight loss greater than or equal to 5% in the previous 6 months and/or body mass index less than 20 $kg/m^2$.

body weight loss greater than 2% in the previous 3 or 6 months with a BMI<20 body weight loss >2% in the previous 3 or 6 months with an appendicular skeletal muscle index consistent with sarcopenia (males <7.26 $kg/m^2$;
females <5.45 $kg/m^2$)

a multifactorial syndrome characterized by severe body weight, fat and muscle loss and increased protein catabolism due to underlying disease(s).

Early satiety refers to the tendency of a patient to experience fullness or satiety early when consuming a meal.

Fatigue is generally defined as a feeling of weariness, tiredness, or lack of energy. Fatigue can also be defined in terms of patient scores on various assessments or self-evaluations including questions designed to rank feelings of weariness, tiredness, or lack of energy. Specific assessments include the FACIT-F, which contains a 27-item Functional Assessment of Cancer Therapy-General (FACT-G) and a Fatigue Subscale (also referred to herein as the "fatigue domain") consisting of thirteen questions that can be scored 0-4 and measure the patient's perception of fatigue and anemia-related concerns. The FACIT-F and FACT-G questionnaires are described in: The Functional Assessment of Chronic Illness Therapy (FACIT) Measurement System: properties, applications, and interpretation by Webster, K, Cella, D, and Yost, K, Health and Quality of Life Outcomes, volume 1, published 2003; Manir, Indian J Palliat Care. 2012 May-August; 18(2): 109-116; and Minton O, Stone P. A systematic review of the scales used for the measurement of cancer-related fatigue (CRF) Ann Oncol. 2009; 20:17-25. An increase in the patient's score during the course of the therapy indicates an improvement in fatigue.

As reported by Manir et al., FACIT-F scoring is a quality of life assessment tool used to assess cancer treatment related fatigue. Cella D F. Manual of the functional assessment of chronic illness therapy (FACIT) scales. Version 4. Evanston, Ill.: Evanston Northwestern Healthcare. 1997. It has good test-retest reliability (r ranging from 0.82 to 0.92) and is sensitive to change over time. It has also been shown to have convergent and discriminate validity. Cella D F. Manual of the functional assessment of chronic illness therapy (FACIT) scales. Version 4. Evanston, Ill.: Evanston Northwestern Healthcare. 1997; Yellen S B, Cella D F, Webster K, Blendowski C, Kaplan E. Measuring fatigue and other anemia-related symptoms with the Functional Assessment of Cancer Therapy (FACT) measurement system. J Pain Symptom Manage. 1997; 13:63-74. [PubMed: 9095563]; Cella D F, Bonomi A E, Leslie W T, Von Roenn J, Tchekmeydian N S. Quality of life and nutritional well-being, Measurements and relationship. Oncology. 1993; 79(suppl):105-11.

FACIT-F (version 4) is a 40-item self-report instrument. It includes core Functional Assessment of Cancer Therapy-General (FACT-G) scale with 27 items and one additional concern subscale (Fatigue) with 13 items. FACT-G items are divided into four subscale items: (a) Physical Well-being (PWB) (7 items), (b) Social/Family Well-being (SWB)(7 items), (c) Emotional Well-being (EWB) (6 items), and (d) Functional Well-being (FWB) (7 items). FACIT-F scores use a 5-point Likert-type score ranging from "0" (Not at all) to "4" (Very much).

Scores are obtained in each of the special domains and FACT-G score (includes summed score of PWB, SWB, EWB, and FWB). Total FACIT score was obtained by adding additional concern score (Fatigue) with FACT-G. Negatively stated items are reversed by subtracting the response from "4." After reversing proper items, all subscale items are summed to a total, which is the subscale score. For all FACIT scales and symptom indices, the higher the score, the better the Health-related Quality of Life (HRQoL). For missing and unanswered items, subscale scores are prorated as per administration guideline manual of FACIT-F score. This is usually done by using the formula below:

Prorated subscale score=[Sum of item scores]×[$N$ of items in subscale]÷[$N$ of items answered].

When there are missing data, prorating subscale score in this way is acceptable as long as more than 50% of the items were answered (e.g. a minimum of 4 of 7 items, 4 of 6 items, etc.). The total score is then calculated as the sum of the unweighted subscale scores. The FACT scale is considered to be an acceptable indicator of patient quality of life as long as the overall item response rate is greater than 80% (e.g. at least 22 of 27 FACT-G items completed).

The prevalence of fatigue at each measurement point is determined by choosing a cut-off score of <34 in the FACIT-F (additional concern item). Minton O, Stone P. A systematic review of the scales used for the measurement of cancer-related fatigue (CRF) Ann Oncol. 2009; 20:17-25. [PubMed: 18678767]

A four question subset of the Fatigue Subscale, called the Simplified Evaluation for Fatigue (SEF), is also used to determine if the patient is suffering from fatigue, again ranked from 0-4, with questions specifically directed to being too tired to eat, feeling fatigued or weak all over, and being forced to spend time in bed. An increase in the patient's score during the course of the therapy, preferably of at least about 1.0, 1.25, 1.50, 1.75, or 2.0 points from baseline, indicates an improvement in fatigue.

FACT-G includes 4 domains: physical well-being (PWB, seven items), social/family well-being (SWB, seven items), emotional well-being (EWB, six items), and functional well-being (FWB, seven items), which can be scored 0-4. PWB questions are directed to energy levels, nausea, pain, problems with side effects, and feeling ill. SWB questions are directed to social and emotional support from friends, family, and the patient's partner. EWB questions are directed to feelings of sadness, hopelessness and nervousness and concerns about dying and worsening condition. FWB questions are directed to ability to work and enjoy life, ability to sleep, and overall quality of life.

Increasing the survival time refers to increasing the longevity of a patient.

FAACT refers to Functional Assessment of Anorexia Cachexia Therapy (FAACT) Questionnaire. The FAACT Questionnaire is described in: Quality of Life and Nutrition in the Patient with Cancer by Small, W, Carrara, R., Danford, L, Logemann, J, and Cella, D, ACCC's "Integrating Nutrition Into Your Cancer Program, pages 13-14, published March/April 2002. FAACT in the anorexia/cachexia domain refers to the following series of twelve questions that measure patients' perception of and concerns related to appetite, food consumption, weight gain/loss, vomiting, and stomach pain, which can be scored from 0-4.

| ADDITIONAL CONCERNS | Not at all | A little | Some-what | Quite a bit | Very much |
|---|---|---|---|---|---|
| I have a good appetite | 0 | 1 | 2 | 3 | 4 |
| The amount I eat is sufficient to meet my needs | 0 | 1 | 2 | 3 | 4 |
| I am worried about my weight | 0 | 1 | 2 | 3 | 4 |
| Most food tastes unpleasant to me | 0 | 1 | 2 | 3 | 4 |
| I am concerned about how thin I look | 0 | 1 | 2 | 3 | 4 |
| My interest in food drops as soon as I try to eat | 0 | 1 | 2 | 3 | 4 |
| I have difficulty eating rich or "heavy" foods | 0 | 1 | 2 | 3 | 4 |
| My family or friends are pressuring me to eat | 0 | 1 | 2 | 3 | 4 |
| I have been vomiting | 0 | 1 | 2 | 3 | 4 |
| When I eat, I seem to get full quickly | 0 | 1 | 2 | 3 | 4 |
| I have pain in my stomach area | 0 | 1 | 2 | 3 | 4 |
| My general health is improving | 0 | 1 | 2 | 3 | 4 |

A score of 18, 19, 20, 21, 22, 23, 24 or 25 or higher on the FAACT anorexia/cachexia domain can be used to indicate that the patient is suffering from anorexia and/or cachexia; an increase in the patient's score during the course of the therapy, preferably of 2, 3, 4, 5 or more from baseline, indicates an improvement in cachexia. A four-question subset of the FAACT, called the Simplified Evaluation for Appetite (SEA), is also used to measure appetite/eating, again ranking questions from 0-4, with questions specifically directed to appetite, sufficiency of food consumption, pressure by others to eat, and feelings of early satiety, or getting full quickly after starting to eat. An increase in the patient's score during the course of the therapy of at least about 1.0, 1.25, 1.50, 1.75, or 2.0 points from baseline, indicates an improvement in appetite.

FAACT total score refers to the patient's score on the FACT-G added to his score on the FAACT anorexia/cachexia subscale. A FAACT total score of 21, 22, 23, 24, 25, or 26 or higher indicates that the patient has cachexia; an increase in the patient's score during the course of the therapy, preferably of 3, 4, 5 or more from baseline, indicates an improvement in cachexia.

FAACT Trial Outcome Index (TOI) refers to the patient's score on the PWB and FWB subsections of the FACT-G added to his score on the FAACT anorexia/cachexia subscale. A FAACT TOI of greater than 16, 18, 20, 22, or 24 indicates that the patient has cachexia; an increase in the patient's score during the course of the therapy, preferably of 3, 4, 5 or more from baseline, indicates an improvement in cachexia.

FACIT-F total score refers to the patient's score on the FACT-G added to his score on the Fatigue Subscale of the FACIT-F. A FACIT-F total score of 16, 18, 20, 22 or 24 or higher indicates that the patient has fatigue; an increase in the patient's score during the course of the therapy, preferably of 3, 4, 5 or more from baseline, indicates an improvement in fatigue.

FACIT-F TOI refers to the patient's score on the PWB and FWB subsections of the FACT-G added to his score on the Fatigue Subscale of the FACIT-F. A FACIT-F TOI of 16, 18, 20, 22 or 24 or higher indicates that the patient has fatigue; an increase in the patient's score during the course of the therapy, preferably of 3, 4, 5 or more from baseline, indicates an improvement in fatigue.

Stage III non-small cell lung cancer includes both Stage IIIA and IIIB as defined by the National Cancer Institute at the National Institutes of Health. Stage IV NSCLC is also defined by the National Cancer Institute at the National Institutes of Health. Criteria for staging NSCLC can be found at National Comprehensive Cancer Network. NCCN Clinical Practice Guidelines in Oncology: Non-small cell lung cancer. Version 2.2013. Available at http://www.nccn.org/professionals/physician_gls/pdf/nscl.pdf. Accessed Sep. 24, 2013.

ECOG (Eastern Cooperative Oncology Group) Status refers to scales and criteria used by doctors and researchers to assess how a patient's disease is progressing, assess how the disease affects the daily living abilities of the patient, and determine appropriate treatment and prognosis.

| ECOG PERFORMANCE STATUS* | |
| --- | --- |
| Grade | ECOG |
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all self care but unable to carry out any work activities. Up and about more than 50% of waking hours |
| 3 | Capable of only limited self care, confined to bed or chair more than 50% of waking hours |
| 4 | Completely disabled. Cannot carry on any self care. Totally confined to bed or chair |
| 5 | Dead |

*Oken, M.M., Creech, R.H., Tormey, D.C., Horton, J., Davis, T.E., McFadden, E.T., Carbone, P.P.: Toxicity And Response Criteria Of The Eastern Cooperative Oncology Group. Am J Clin Oncol 5:649-555, 1982.

Discussion

As mentioned above, the inventors have developed several methods for treating disorders and conditions associated with cancer cachexia using anamorelin. In a first principal embodiment, the invention provides a method of treating cachexia in a human cancer patient by increasing the lean body mass of said patient, comprising administering to said patient a therapeutically effective amount of anamorelin for a therapeutically effective period of time.

In a second principal embodiment, the invention provides a method of treating cachexia in a human cancer patient suffering from unresectable Stage III or IV non-small cell lung cancer and cachexia as defined by body weight loss greater than or equal to 5% in the previous 6 months or body mass index less than 20 kg/m$^2$, by increasing the lean body mass of said patient, comprising administering to said patient a therapeutically effective amount of anamorelin for a therapeutically effective period of time.

In a third principal embodiment the invention provides a method of treating early satiety resulting from cancer cachexia in a human cancer patient comprising administering to said patient a therapeutically effective amount of anamorelin for a therapeutically effective period of time.

In a fourth principal embodiment the invention provides a method of treating fatigue resulting from cancer cachexia in a human cancer patient comprising administering to said patient a therapeutically effective amount of anamorelin for a therapeutically effective period of time. The fatigue can derive from a number of sources, including depression, anemia, sarcopenia, anorexia, vomiting-related malnutrition, chemo-toxicity, opioid use, or sleep disturbances, or any combination of the foregoing conditions.

In a fifth principal embodiment the invention provides a method of increasing the survival time of a terminally ill cancer patient comprising administering to said patient a therapeutically effective amount of anamorelin for a therapeutically effective period of time.

In a sixth principal embodiment the invention provides a method of improving quality of life as measured by FAACT in the anorexia/cachexia domain in a human cancer patient comprising administering to said patient a therapeutically effective amount of anamorelin for a therapeutically effective period of time.

In a seventh principal embodiment the invention provides a method of increasing total body mass, lean body mass, and fat mass in a human patient suffering from cancer cachexia comprising administering to said patient a therapeutically effective amount of anamorelin for a therapeutically effective period of time. The method is preferably practiced in a patient who has lost total body mass, lean body mass, as well as fat mass over the preceding three or six months. The patient might have lost greater then 1, 2, 3, 4 or even 5% of total body mass, lean body mass, and fat mass, in any combination of percentages, but has most preferably lost greater than 2% of total body mass, lean body mass, and fat mass over the previous six months.

In an eighth principal embodiment, the invention provides a method of improving quality of life in a human cancer patient comprising administering to said patient a therapeutically effective amount of anamorelin for a therapeutically effective period of time, wherein the quality of life improvement is measured by:
FAACT (Total Score or TOI);
SEA Score;
SEF Score;
FACIT-G (Total Score or TOI); or
FACIT-F (Total Score or TOI).

In any of the foregoing principal embodiments, the administration is preferably oral, and the drug is preferably administered once daily.

In any of the foregoing principal embodiments, the patient has in various subembodiments suffered in the previous three, six months or twelve months:
anorexia, early satiety, weight loss, muscle wasting, anemia, or oedema, or 3, 4, 5 or all of these conditions;
body weight loss greater than or equal to 5% and/or body mass index less than 20 kg/m$^2$;
body weight loss greater than 2, 3, 4 or 5% with a BMI<20;
greater than 2, 3, 4 or 5% body weight, fat and muscle loss with a BMI<20;
body weight loss greater than 2, 3, 4, or 5% with an appendicular skeletal muscle index consistent with sarcopenia (males <7.26 kg/m$^2$; females <5.45 kg/m$^2$);
greater than 2, 3, 4 or 5% body weight, fat and muscle loss and increased protein catabolism;
a reduction of 3, 4, or 5 points in FAACT, FACIT-F, FACT-G, SEF, FAACT in the anorexia/cachexia domain, FAACT TOI, FACIT-F TOI, or FACT-G TOI.

Any of the foregoing principal embodiments can be performed in any type of cancer, but each of the methods is preferably practiced in a cancer of the type which is generally associated with cancer cachexia. Non-limiting examples of relevant cancers include, e.g., breast cancer, prostate cancer, multiple myeloma, transitional cell carcinoma, lung cancer (e.g., non-small cell lung cancer (NSCLC)), renal cancer, thyroid cancer and other cancers causing hyperparathyroidism, adenocarcinoma, leukemia (e.g., chronic myeloid leukemia, acute myeloid leukemia, chronic lymphocytic leukemia, acute lymphocytic leukemia), lymphoma (e.g., B cell lymphoma, T cell lymphoma, non-Hodgkin's lymphoma, Hodgkin's lymphoma), head and neck cancer, esophageal cancer, stomach cancer, colon cancer, intestinal cancer, colorectal cancer, rectal cancer, pancreatic cancer, liver cancer, cancer of the bile duct, cancer of the gall bladder, ovarian cancer, uterine endometrial cancer, vaginal cancer, cervical cancer, bladder cancer, neuroblastoma, sarcoma, osteosarcoma, malignant melanoma, squamous cell cancer, bone cancer, including both primary bone cancers (e.g., osteosarcoma, chondrosarcoma, Ewing's sarcoma, fibrosarcoma, malignant fibrous histiocytoma, adamantinoma, giant cell tumor, and chordoma) and secondary (metastatic) bone cancers, soft tissue sarcoma, basal cell carcinoma, angiosarcoma, hemangiosarcoma, myxosarcoma, liposarcoma, osteogenic sarcoma, angiosarcoma, endotheliosarcoma, lymphangiosarcoma, lymphangioendotheliosarcoma, synovioma, testicular cancer, uterine cancer, gastrointestinal cancer, mesothelioma, leiomyosarcoma, rhabdomyosarcoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, choriocarcinoma, seminoma, embryonal carcinoma, Wilms' tumor, epithelial carcinoma, glioma, glioblastoma, astrocytoma, medulloblastoma, craniopharyngioma, ependymoma, pinealoma, hemangioblastoma, acoustic neuroma, oligodendroglioma, meningioma, retinoblastoma, medullary carcinoma, thymoma, sarcoma, etc. In a preferred embodiment the cancer is non-small cell lung cancer (NSCLC), more preferably non-resectable Stage III or IV NSCLC.

The patient may or may not be receiving chemotherapy in any of the foregoing principal embodiments. Non-limiting examples of chemotherapy agents include antimetabolites such as pyrimidine analogs (e.g., 5-fluorouracil [5-FU], floxuridine, capecitabine, gemcitabine and cytarabine) and purine analogs, folate antagonists and related inhibitors (e.g., mercaptopurine, thioguanine, pentostatin and 2-chlorodeoxyadenosine (cladribine)); antiproliferative/antimitotic agents including natural products such as vinca alkaloids (e.g., vinblastine, vincristine, and vinorelbine), microtubule disruptors such as taxanes (e.g., paclitaxel, docetaxel), vincristin, vinblastin, nocodazole, epothilones and navelbine, epidipodophyllotoxins (e.g., etoposide, teniposide), DNA damaging agents (e.g., actinomycin, amsacrine, anthracyclines, bleomycin, busulfan, camptothecin, carboplatin, chlorambucil, cisplatin, nedaplatin, cyclophosphamide, cytoxan, dactinomycin, daunorubicin, doxorubicin, epirubicin, aclarubicin, purarubicin, hexamethyhnelamineoxaliplatin, iphosphamide, melphalan, merchlorehtamine, mitomycin, mitoxantrone, nitrosourea, nimustine, ranimustine, estramustine, plicamycin, procarbazine, taxol, taxotere, teniposide, triethylenethiophosphoramide and etoposide (VP16)); antibiotics (e.g., dactinomycin (actinomycin D), daunorubicin, doxorubicin (adriamycin), idarubicin, anthracyclines, mitoxantrone, bleomycins, plicamycin (mithramycin), pleomycin, peplomycin, mitomycins (e.g., mitomycin C), actinomycins (e.g., actinomycin D), zinostatinstimalamer); enzymes (e.g., L-asparaginase); neocarzinostatin; antiplatelet agents; antiproliferative/antimitotic alkylating agents such as nitrogen mustards (e.g., mechlorethamine, cyclophosphamide and analogs, imidazol carboxamide, melphalan, chlorambucil, nitrogen mustard-N-oxide hydrochloride, ifosfamide), ethylenimines and methylmelamines (e.g., hexamethylmelamine, thiotepa, carboquone, triethylene thiophospharamide), alkyl sulfonates (e.g., busulfan, isoprosulfan tosylate), nitrosoureas (e.g., carmustine (BCNU) and analogs, streptozocin), trazenesdacarbazinine (DTIC); epoxide type compounds (e.g., mitobronitol); antiproliferative/antimitotic antimetabolites such as folic acid analogs (e.g., methotrexate); platinum coordination complexes (e.g., cisplatin, carboplatin, oxaliplatin), procarbazine, hydroxyurea, mitotane, aminoglutethimide; hormones, hormone analogs (e.g., estrogen, tamoxifen, goserelin, bicalutamide, nilutamide) and aromatase inhibitors (e.g., letrozole, anastrozole); anticoagulants (e.g., heparin, synthetic heparin salts and other inhibitors of thrombin); fibrinolytic agents (e.g., tissue plasminogen activator, streptokinase and urokinase), aspirin, dipyridamole, ticlopidine, clopidogrel, abciximab; antimigratory agents; antisecretory agents (e.g., breveldin); immunosuppressives (e.g., cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blockers; nitric oxide donors; antisense oligonucleotides; antibodies (e.g., trastuzumab); cell cycle inhibitors and differentiation inducers (e.g., tretinoin); mTOR inhibitors, topoisomerase inhibitors (e.g., doxorubicin (adriamycin), amsacrine, camptothecin, daunorubicin, dactinomycin, eniposide, epirubicin, etoposide, idarubicin, mitoxantrone, topotecan, irinotecan); growth factor signal transduction kinase inhibitors; mitochondrial dysfunction inducers; chromatin disruptors; sobuzoxane; tretinoin; pentostatin; flutamide; porphimer natrium; fadrozole; procarbazine; aceglatone, and mitoxantrone.

In any of the foregoing principal embodiments, the therapeutically effective amount of anamorelin can vary across a range of suitable doses depending on the health of the subject, the desired response, the dosage form and the route of administration. In a preferred subembodiment the therapeutically effective amount is from about 10 to about 500 mg/day of anamorelin, preferably from 25 to 300 mg/day, more preferably 50 to 150 mg/day. In an even more preferred embodiment the dose is administered as a single administration once per day, preferably before the first meal of the day.

In any of the foregoing principal embodiments, the therapeutically effective amount of anamorelin is preferably effective to increase lean body mass in said patient, or to increase the total body mass and lean body mass of the patient, or to increase the total body weight, lean body mass and fat mass of the patient.

A particularly surprising aspect of any of the foregoing principal embodiments is the sustainability of the effect observed in cancer patients, which is reflected in the therapeutically effective period of administration. This sustainability can be observed in patients having any ECOG score, including an ECOG score greater than about 2.0, 2.5, 3, 3.5 or 4. In any of the foregoing embodiments the therapeutically effective period of time is preferably twelve weeks. In alternative embodiments, the therapeutically effective period is 3, 6, 9, 12, 13, 15, 18, 21 or 24 weeks, or any range defined by these endpoints, such as 13 to 24 weeks. When a particular period of time is given, it will be understood that anamorelin can be administered for a greater period of time, as long as the required response is observed during the period given. It will further be understood that the response to treatment can be observed beyond the prescribed period. I.e., administration for 12 weeks includes administration for at least 12 weeks, and treatment for 12 weeks means treatment for at least 12 weeks.

The treatment effect in any of the foregoing principal embodiments can be correlated or not correlated with IGF-1 levels and/or IGFBP-3 levels. In one embodiment for any of the foregoing methods the treatment effect is not correlated with increases in IGF-1 levels. In another embodiment the treatment effect is not correlated with increases in IGFBP-3 levels.

Any of the foregoing principal embodiments can be practiced based on the patient's ECOG status. Thus, for example, any of the embodiments can be practiced in a patient having a performance status on the ECOG scale of 2, 2.5, 3, 4 or higher, i.e. from 2 to 4, or 2, 3 or 4.

Any of the foregoing principal embodiments may also be practiced based on age. Thus, for example, any of the foregoing methods may be practiced in an individual greater than 50, 55, 60, 65 or 70 years of age. In one particular embodiment the invention is practiced in a population of patients ranging from 50 to 90, who in one embodiment are suffering from lung cancer.

Any of the foregoing principal embodiments may further be divided based on BMI status. Thus, for example, any of the foregoing methods may be practiced in an individual having a BMI less than 22, 20, 19, 18.5 or even 18. Alternatively, any of the foregoing embodiments may be practiced in an individual having a BMI greater than 14, 16, 18 or 20.

Any of the foregoing embodiments may also be limited based on other parameters. Thus, in any of the foregoing principal embodiments the cancer can be defined by a squamous tumor histology. In any of the foregoing principal embodiments the patient's cancer may or may not have metastacized. In any of the foregoing principal embodiments the patient may or may not be receiving chemotherapy and/or radiotherapy. In any of the foregoing principal embodiments the patient may or may not be receiving opioids.

Dosage Forms/Routes of Administration

Pharmaceutical compositions for preventing and/or treating a subject are further provided comprising a therapeutically effective amount of a compound of formula (I), or a pharmaceutically acceptable salt or adduct thereof, and one or more pharmaceutically acceptable excipients.

A "pharmaceutically acceptable" excipient is one that is not biologically or otherwise undesirable, i.e., the material can be administered to a subject without causing any undesirable biological effects or interacting in a deleterious manner with any of the other components of the pharmaceutical composition in which it is contained. The carrier can be selected to minimize any degradation of the active ingredient and to minimize any adverse side effects in the subject, as would be well known to one of skill in the art. The carrier can be a solid, a liquid, or both.

The disclosed compounds can be administered by any suitable route, preferably in the form of a pharmaceutical composition adapted to such a route, and in a dose effective for the treatment or prevention intended. The active compounds and compositions, for example, can be administered orally, rectally, parenterally, ocularly, inhalationaly, or topically. In particular, administration can be epicutaneous, inhalational, enema, conjunctival, eye drops, ear drops, alveolar, nasal, intranasal, vaginal, intravaginal, transvaginal, ocular, intraocular, transocular, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc.

EXAMPLES

The following two studies were conducted to evaluate the effect of anamorelin on LBM in patients with NSCLC, as well as to determine its effects on body weight, patient concerns regarding cachexia and fatigue, and overall survival. Efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1 Anamorelin HCl in the Treatment of Non-Small Cell Lung Cancer-Cachexia (NSCLC-C): A Randomized, Double-Blind, Placebo-Controlled, Multicenter, Phase III Study to Evaluate the Safety and Efficacy of Anamorelin HCl in Patients with NSCLC-C(Romana 1)

Key features of the Romana 1 study are as follows:
DESIGN: randomized, double-blind, placebo-controlled, multicenter, phase 3 study to evaluate the safety and efficacy of anamorelin HCl (anamorelin) in patients with NSCLC-Cachexia (59 sites; 15 countries)
PRIMARY ENDPOINT: Lean body mass (LBM) by DXA
SECONDARY ENDPOINTS:
  Key: pooled overall survival, Anorexia/Cachexia sub-domain, Fatigue sub-domain, Simplified Evaluation of Appetite (SEA), and Simplified Evaluation of Fatigue (SEF)
  Other: Body weight, study specific overall survival, FAACT/FACIT-F trial outcome index (TOI) and total scores, additional LBM analyses
EXPLORATORY ENDPOINTS: Hunger Assessment Scale (HAS), Karnofsky (KPS), responder analyses; Population pharmacokinetics (PK) in 90 patients
STUDY POPULATION: advanced NSCLC (unresectable Stage III or IV) and cachexia ($\geq 5\%$ body weight within 6 months or screening BMI<20 kg/m$^2$)
SAMPLE SIZE: 484 patients; randomization ratio 2:1 (anamorelin:placebo)
DOSING: placebo or 100 mg anamorelin for 12 weeks
SAFETY ASSESSMENTS: Adverse events (AEs), labs, vitals, ECGs FIG. 1 is a graphical representation of the results of the primary efficacy study (lean body mass), particularly the median change from baseline in the ITT population. Panel A depicts changes in LBM in patients receiving placebo (PBO) vs. anamorelin over the 12-week study period. Patients receiving anamorelin showed higher increases in LBM relative to patients receiving placebo.

TABLE 1

Analysis of Change from Baseline Over 12 Weeks in Lean Body Mass-ITT Population.

|  | Lean Body Mass | |
| --- | --- | --- |
|  | Placebo (N = 161) | 100 mg anamorelin (N = 323) |
| N* | 158 | 316 |
| Median | −0.44 | 1.10 |
| 95% CI | (−0.88, 0.20) | (0.76, 1.42) |
| Median |  | 1.54 |
| P-value** |  | <0.0001 |

*Sample size takes into account those who were excluded due to missing baseline values and/or missing death dates.
**P-value is obtained from Wilcoxon Rank-sum test, taking into account missing post-baseline values (i.e., imputation), whereby lower ranks represent worse outcomes. The ranking order is determined by the average change from baseline in LBM at Week 6 and Week 12 with imputed values, and also by the survival date.

As shown in Table 1 above, for LBM, there were statistically significant (based on unadjusted p-values) effects favoring anamorelin. This is true among all subgroups except for age >65, BMI<18.5, ECOG 2 and female, which may be due to small sample size in these subgroups.

Key secondary endpoints were measured in the MITT population, with a brief summary of results as follows. These results are further explained and demonstrated in the following Figures and Tables.

In terms of health-related quality of life measurements (HR-QoL), results from the anorexia/cachexia domain of the FAACT assessment showed anamorelin provides statistically significant and clinically meaningful improvements in patient concerns related to these issues. Patients in the anamorelin group also had statistically significant and clinically meaningful improvements in regard to the SEA assessment, which focuses on feelings of early satiety, appetite, food consumption, and pressure by others to eat. HR-QoL assessments related to fatigue, listlessness and weakness, as measured by the Fatigue domain of FACIT-F, showed statistically significant improvements at Weeks 9 and 12. Some subgroups showed a trend of improvement in the FACIT-F assessment with anamorelin treatment. There was an overall trend of improvement in the SEF assessment, which focuses on feelings of fatigue and general weakness. Patients in some subgroups also had trends of improvement in regard to the SEF assessment.

Figure 2A:
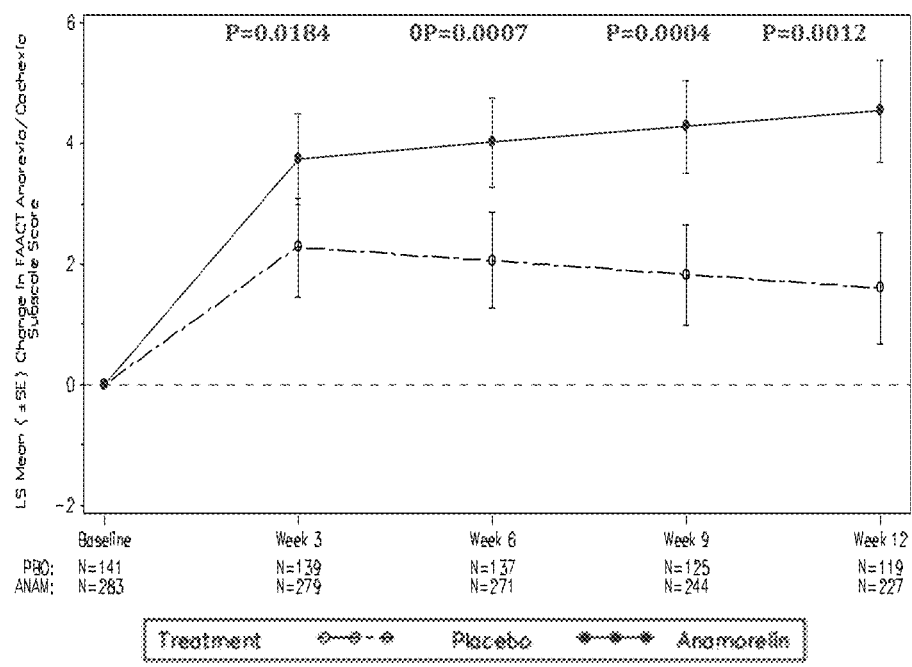
FIGS. 2A-B are graphical representations of patient symptoms and concerns related to cachexia as measured by change in FAACT anorexia/cachexia subscore and SEA score, specifically the treatment comparison of change from baseline at each visit in the modified intent to treat ("MITT") population in patients receiving anamorelin and placebo in Romana 1. Data shown are from a mixed-effects pattern-mixture model.
Figure 2B:
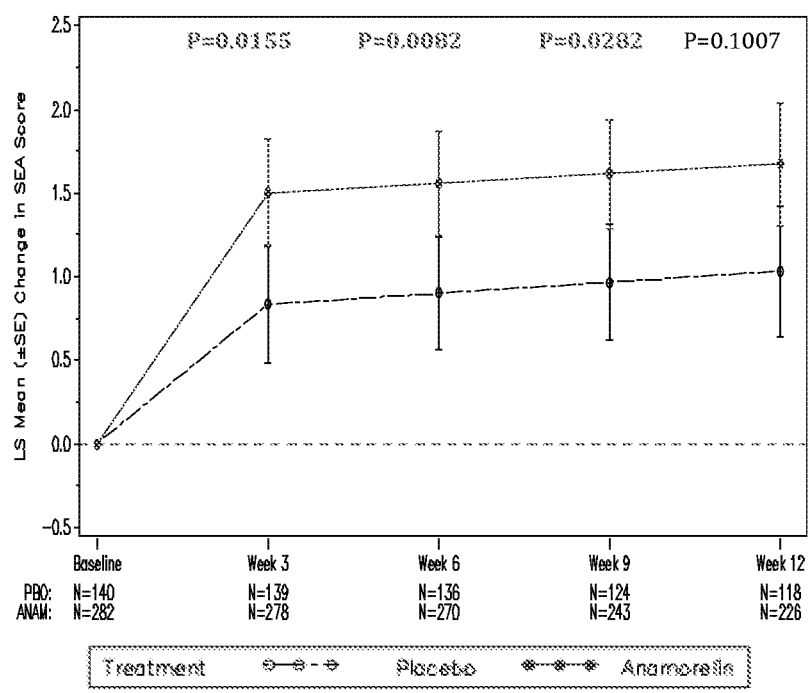

FIGS. 2A-B are graphical representations of patient symptoms and concerns related to cachexia as measured by FAACT anorexia/cachexia subscore and SEA score, specifically the treatment comparison of change from baseline at each visit in the MITT population. Panel A shows the results for the anorexia/cachexia domain of FAACT in the MITT population over the 12-week study period, including the statistical significance of any differences in results from patients treated with placebo vs. anamorelin (p values). Patients in the anamorelin group showed statistically significant and clinically meaningful improvements in QoL related to concerns over cachexia. Panel B shows the results for the SEA score of FAACT in the MITT population over the 12-week study period, including the statistical significance of any differences in results from patients treated with placebo vs. anamorelin (p values). Patients in the anamorelin group showed statistically significant and clinically meaningful improvements in QoL concerns measured by the SEA, such as improvements in general appetite and consuming sufficient amounts of food, and decreases in early satiety and pressure by others to eat. Results are also presented below in Table 2. Data shown are from a mixed-effects pattern-mixture model.

TABLE 2

Analysis of Change in Patient Symptoms and Concerns Related to Anorexia/Cachexia from Baseline Over 12 Weeks-MITT Population.

|  | Anorexia/Cachexia Domain | | SEA Score | |
| --- | --- | --- | --- | --- |
|  | Placebo (N = 141) | 100 mg anamorelin (N = 284) | Placebo (N = 141) | 100 mg anamorelin (N = 284) |
| N | 141 | 282 | 140 | 281 |
| LS Mean (SE) | 1.92 (0.805) | 4.12 (0.752) | 0.92 (0.339) | 1.57 (0.317) |
| | Treatment Difference (anamorelin vs. placebo) | | | |
| LS Mean (SE) | 2.21 (0.617) | | 0.65 (0.262) | |
| 95% CI | (0.99, 3.42) | | (0.14, 1.16) | |
| P-value | 0.0004 | | 0.0134 | |

*Note,
importance difference is estimated to be ~3 points for anorexia/cachexia domain and ~1 point for SEA score, and both were met with anamorelin treatment.

Figure 3A:
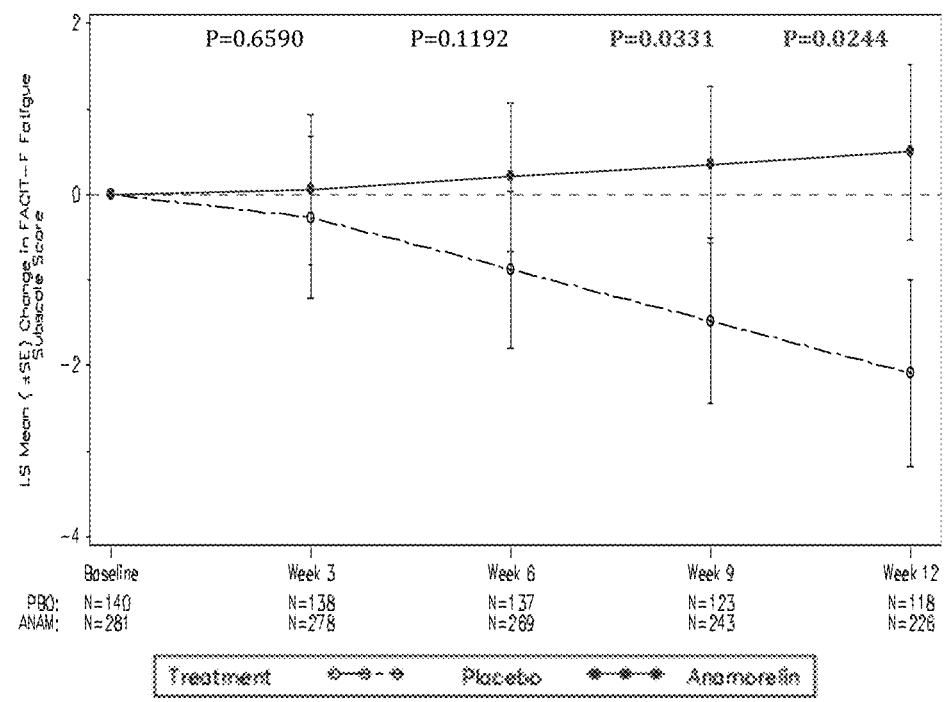
FIGS. 3A-B are graphical representations of patient symptoms and concerns related to fatigue as measured by change in FACIT-F fatigue subscore and SEF score, specifically the treatment comparison of change from baseline at each visit in the MITT population in patients receiving anamorelin and placebo in Romana 1. Data shown are from a mixed-effects pattern-mixture model.
Figure 3B:
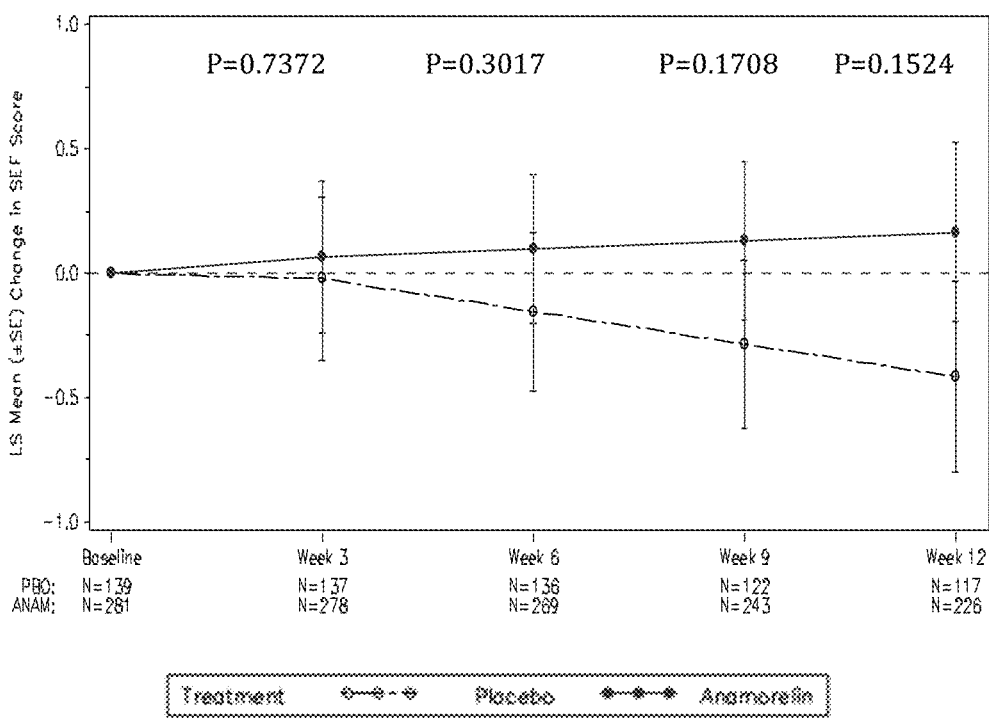

FIGS. 3A-B are graphical representations of patient symptoms and concerns related to fatigue as measured by FACIT-F fatigue subscore and SEF score, specifically the treatment comparison of change from baseline at each visit in the MITT population. Panel A represents the results for the Fatigue Domain of FACIT-F assessment over the 12-week study period in MITT patients, including the statistical significance of any differences in results from patients treated with placebo vs. anamorelin. As can be seen in this panel, statistically significant improvements in the assessment were present at Weeks 9 and 12 in anamorelin patients versus those on placebo. Subgroups of interest receiving anamorelin showed trends of improvement in their fatigue levels. Panel B represents the results for the SEF score of FACIT-F assessment over the 12-week study period in MITT patients, including the statistical significance of any differences in results from patients treated with placebo vs. anamorelin. Here, there was an overall small trend of improvement among anamorelin patients in terms of lower fatigue, lower overall feelings of weakness, and lower amounts of time spent in bed; subgroups showed these trends of improvement as well. Results are also presented in Table 3 below, and specific findings for subgroups are also presented below. Data shown in FIGS. 3A-B are from a mixed-effects pattern-mixture model.

TABLE 3

Patient Symptoms and Concerns Related to Fatigue-Analysis of Change from Baseline Over 12 Weeks in MITT Population.

| | Fatigue Domain | | SEF Score | |
|---|---|---|---|---|
| | Placebo (N = 141) | 100 mg anamorelin (N = 284) | Placebo (N = 141) | 100 mg anamorelin (N = 284) |
| N | 141 | 282 | 139 | 280 |
| LS Mean (SE) | −1.91 (0.933) | 0.26 (0.886) | −0.23 (0.325) | 0.11 (0.309) |
| | Treatment Difference (anamorelin vs. placebo) | | | |
| LS Mean (SE) | 1.45 (0.752) | | 0.33 (0.265) | |
| 95% CI | (−0.02, 2.93) | | (−0.19, 0.85) | |
| P-value | 0.0537 | | 0.2098 | |

Subgroup analyses of the above data regarding the change from baseline in Fatigue Domain of FACIT-F in the MITT population shows a trend of improvement in subgroups. Specific trends included the following subgroups. In a subgroup of patients aged 65 years and younger with concomitant opioid use and ECOG 2 (at Weeks 9 and 12), and BMI≤18.5 improvement at Week 3, 6 and at Week 9, 12 patients showed statistically significant improvement.

In addition, the following subgroup trends were also observed: 1) among patients with no-concomitant opioid use, a smaller overall improvement trend was noted; 2) among patients with ECOG 0-1, a gap increase between placebo and anamorelin through Week 3, 6, 9 to 12 was noted; 3) among patients with BMI>18.5, there was a smaller improvement trend from Week 3 to 12; and 4) a general improvement trend in males from Week 3 to 6 was seen (the improvement was statistically significant at Week 9, with a borderline change at Week 12).

Subgroup analyses of the above data regarding the change from baseline in Simplified Evaluation of Fatigue (SEF) in the MITT population show an overall small trend of improvement in subgroups in terms of fatigue and overall weakness. The following subgroup trends were observed: 1) concomitant opioid use showed a small trend of improvement; and 2) patients with BMI≤18.5 showed improvement trend over 12 Weeks (statistically significant at Week 3 and 6).

Other secondary endpoints measured in the MITT population, along with results, included the following:

Body Weight: Statistically significant and clinically meaningful improvements were seen in anamorelin patients versus those receiving placebo.

Other LBM Analyses: Percentage change from baseline in LBM were measured, with LBM showing consistent improvement throughout the 12-week study.

Other FAACT/FACIT-F Analyses: FAACT TOI and total score showed statistically significant and clinically meaningful improvements for TOI, with a trending benefit for the total score among the anamorelin patients. This indicates that anamorelin treatment improves patient concerns over appetite, food consumption, early satiety, and pain or vomiting. The FACIT-F TOI and total score also showed a trending benefit among the anamorelin patients. Such improvement indicates that anamorelin treatment improves patient concerns in regard to fatigue and weakness. Overall Survival: Study-specific overall survival—Data pending.

Figure 4:
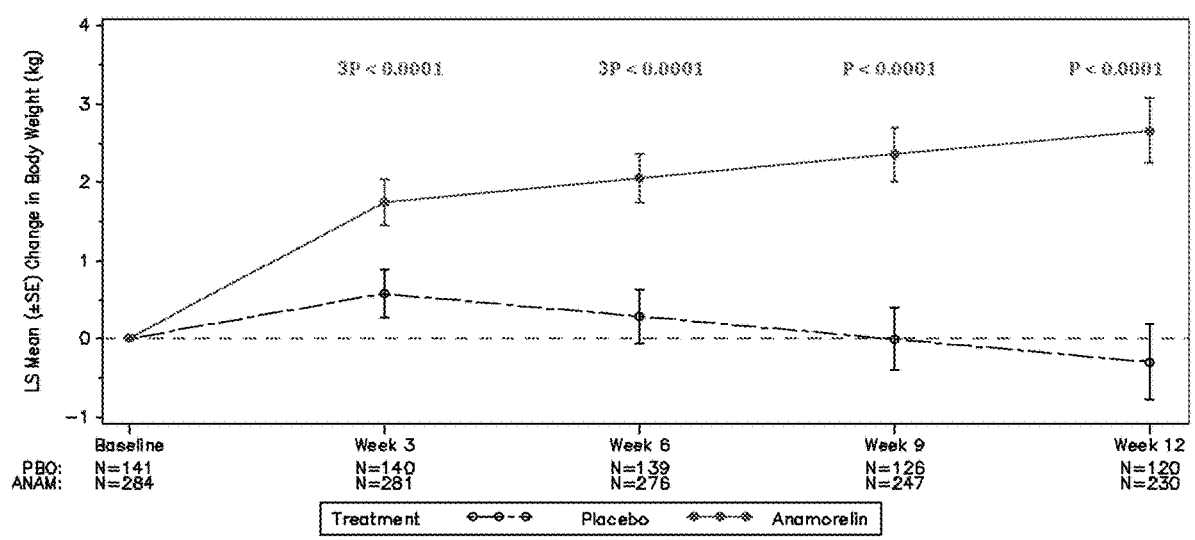
FIG. 4 is a graphical representation of the change from baseline over time in body weight in the MITT population, including the statistical significance of any differences in results from patients treated with placebo vs. anamorelin. Data shown are from a mixed-effects pattern-mixture model.

FIG. 4 is a graphical representation of the change from baseline over time in body weight in the MITT population, including the statistical significance of any differences in results from patients treated with placebo vs. anamorelin. Over the course of the study, patients treated with anamorelin showed a greater, statistically significant increase in body weight versus patients in the placebo group; the results are also presented in Table 4 below. Data shown are from a mixed-effects pattern-mixture model.

TABLE 4

Analysis of Change in Body Weight Over 12 Weeks-MITT Population.

| Overall Change from Baseline | Placebo (N = 141) | 100 mg anamorelin (N = 284) |
|---|---|---|
| N | 141 | 283 |
| LS Mean (SE) | 0.14 (0.363) | 2.20 (0.326) |
| | Treatment Difference (anamorelin vs. placebo) | |
| LS Mean (SE) | 2.07 (0.325) | |
| 95% CI | (1.43, 2.70) | |
| P-value | <0.0001 | |

Figure 5A:
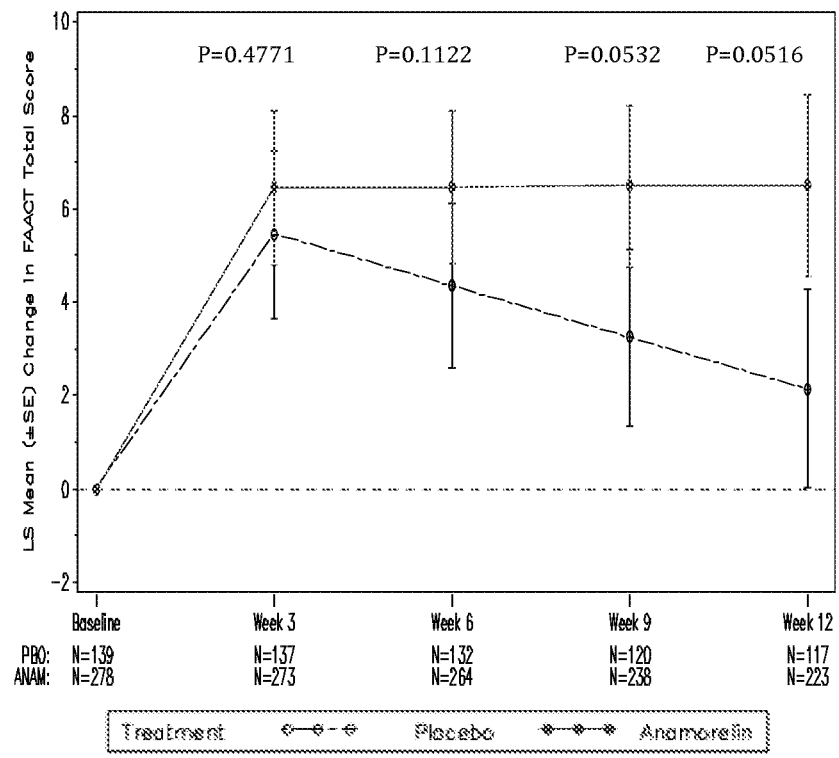
FIGS. 5A-B are graphical representations of health-related Quality of Life changes from baseline in FAACT Total and TOI (Total Outcome Index) in the MITT population in Romana 1. Data shown are from a mixed-effects pattern-mixture model.
Figure 5B:
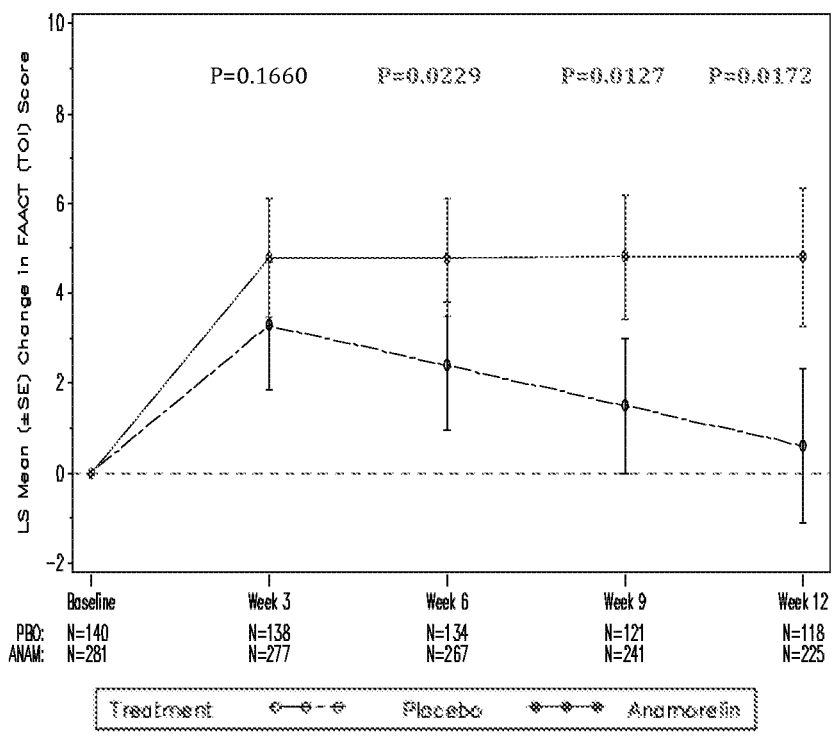

FIGS. 5A-B are graphical representations of health-related Quality of Life changes from baseline in FAACT Total and TOI (Total Outcome Index) in the MITT population. Panel A represents the results for the FAACT Total assessment over the 12-week study period in MITT patients, including the statistical significance of any differences in results from patients treated with placebo vs. anamorelin (p-values). The overall treatment difference for the FACCT Total was 2.67±1.459; p=0.0673. Panel B represents the results for the FAACT TOI assessment over the 12-week study period in MITT patients, including the statistical significance of any differences in results from patients treated with placebo vs. anamorelin (p-values). The overall treatment difference for the FAACT TOI assessment was 2.86±1.161; p=0.0140. As mentioned above, FAACT TOI showed statistically significant and clinically meaningful improvements, and there was a trending benefit for the total score among the anamorelin patients, indicating that anamorelin treatment improves patient concerns over appetite, food consumption, early satiety, and pain or vomiting. Data shown are from a mixed-effects pattern-mixture model.

Figure 6A:
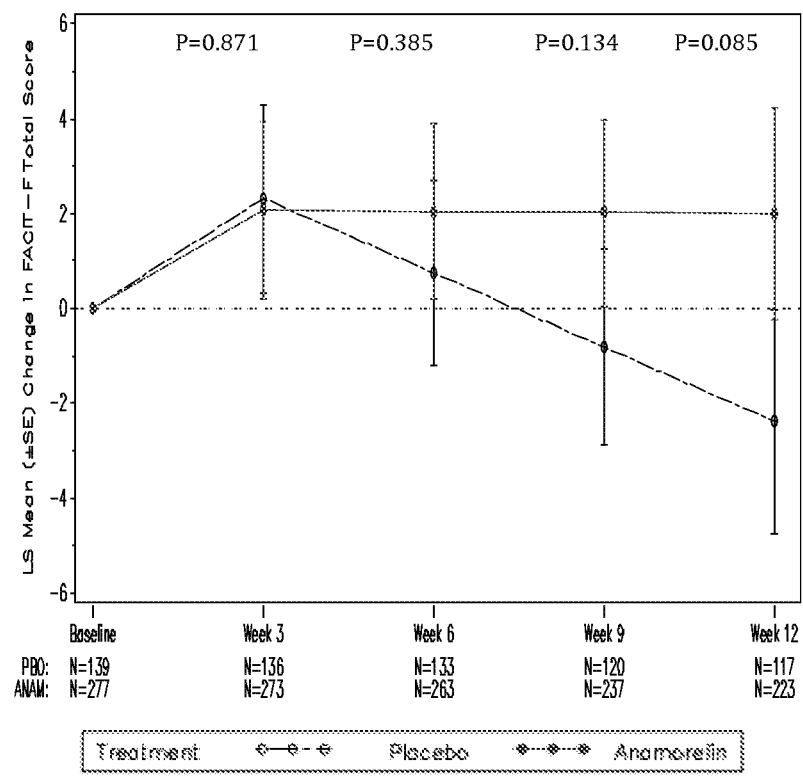
FIGS. 6A-B are graphical representations of health-related Quality of Life change from baseline in FACIT Total and TOI (Total Outcome Index) in the MITT population in Romana 1. Data shown are from a mixed-effects pattern-mixture model.
Figure 6B:
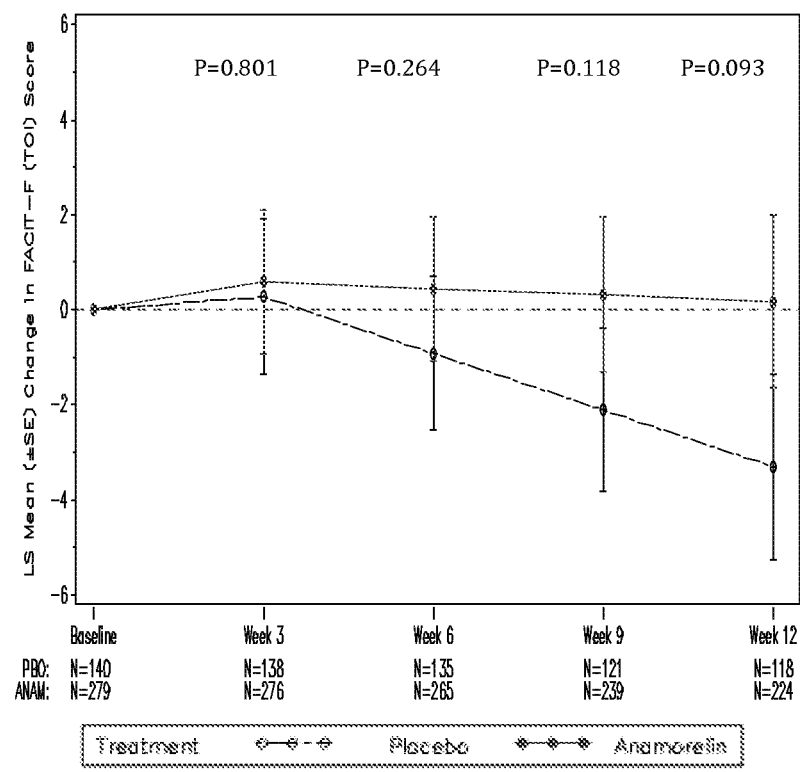

FIGS. 6A-B are graphical representations of health-related Quality of Life change from baseline in FACIT Total and TOI (Total Outcome Index) in the MITT population. Panel A represents the results for the FACIT Total assessment over the 12-week study period in MITT patients, including the statistical significance of any differences in results from patients treated with placebo vs. anamorelin (p-values). The overall treatment difference for the FACIT Total was 2.07±1.651; p=0.2100. Panel B represents the results for the FACIT TOI assessment over the 12-week study period in MITT patients, including the statistical significance of any differences in results from patients treated with placebo vs. anamorelin (p-values). The overall treatment difference for the FACIT TOI assessment was 1.90±1.358; p=0.1615. As mentioned above, the FACIT-F Total and TOI showed a trending benefit among the anamorelin patients. Such improvement indicates that anamorelin treatment improves patient concerns in regard to fatigue and weakness. Data shown are from a mixed-effects pattern-mixture model.

The Romana 1 study yielded the following overall conclusions regarding efficacy of anamorelin treatment. Baseline demographics were balanced (N=484). Overall, median age=62 yr, male (76%), ECOG=2 (18.6%), metastatic (76.4%), and prior weight loss >10% (39.5%). Over 12 weeks, anamorelin significantly increased LBM with respect to placebo (median change from baseline of 1.10 kg [95% CI 0.76, 1.42] vs. −0.44 kg [95% CI −0.88, 0.20]; p<0.0001). Increases in lean body mass (LBM) was found to be statistically significant (p<0.0001).

In terms of secondary efficacy, body weight was significantly increased in patients who received anamorelin versus those on placebo (2.20±0.3 vs. 0.14±0.4 kg; p<0.0001). The FAACT assessment trial outcome index (TOI), anorexia/cachexia domain and Simplified Evaluation of Appetite (SEA) scores, which measured changes in appetite, early satiety, and food consumption, were significantly increased and exceeded minimally important difference thresholds, while total scores showed trending benefits for patients receiving anamorelin versus those in the placebo group. The FACIT-F assessment fatigue domain was statistically significant at Weeks 9 and 12; Simplified Evaluation of Fatigue (SEF), TOI and total scores were not statistically different from placebo, but general trends of improvement with anamorelin were noted. Specifically, patient symptoms and concerns regarding fatigue and weakness appeared to stabilize in the anamorelin arm and worsen in the placebo arm over time, attaining statistically significant differences in FACIT-F scores at week 9 (0.33±0.9 vs. −1.50±1.0; p=0.0331) and week 12 (0.48±1.0 vs. −2.10±1.0; p=0.0244). Over the entire 12 week treatment period, the difference between treatments did not reach statistical significance (1.45+0.8; p=0.0537); the trend favored anamorelin. FAACT scores significantly improved over 12 weeks in anamorelin vs. placebo arms (FAACT scores of 4.12±0.8 vs. 1.92±0.8; p=0.0004).

Trends of improvement in specific patient subgroups include: 1) age less than 65 years; 2) concomitant opioid use; 3) ECOG 2 at Week 9, 12; and 4) BMI<18.5.

Overall, the study shows that anamorelin treatment for 12 weeks was well tolerated, and that the anamorelin therapy increased LBM and body weight while reducing CACS symptoms/concerns in advanced NSCLC patients with cachexia. These increases were highly statistically significant, and appeared to continue to increase with longer exposure. Anamorelin also stabilized patient symptoms/concerns related to fatigue over the 12 weeks of treatment in addition to a statistically significant treatment difference in fatigue symptoms/concerns at weeks 9 and 12.

Example 2 Anamorelin HCl in the Treatment of Non-Small Cell Lung Cancer-Cachexia (NSCLC-C): A Randomized, Double-Blind, Placebo-Controlled, Multicenter, Phase III Study to Evaluate the Safety and Efficacy of Anamorelin HCl in Patients with NSCLC-C (Romana 2)

Figure 7:
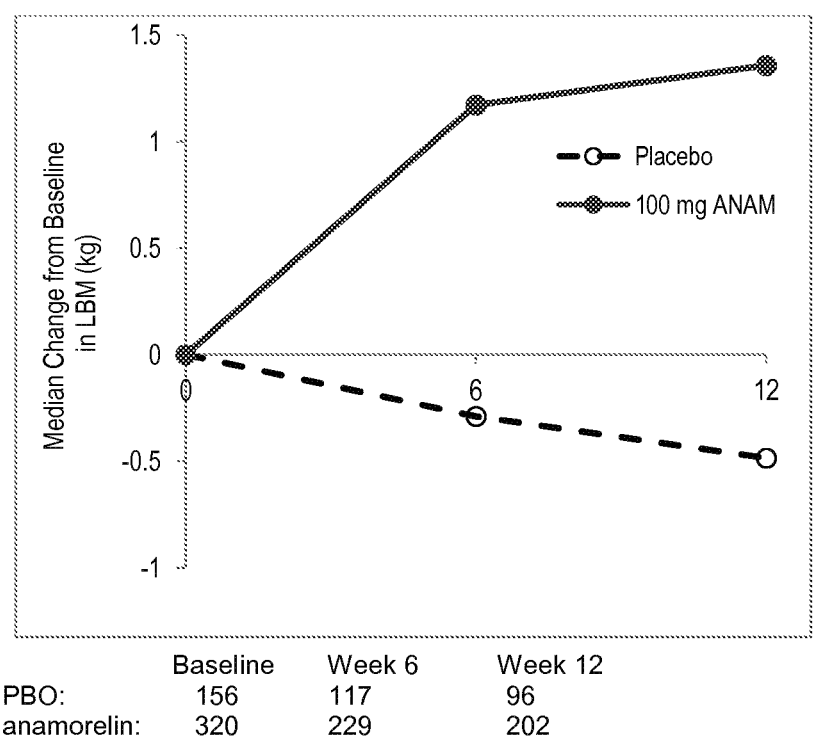
FIG. 7 is a graphical representation of the primary efficacy outcome (lean body mass) in terms of the median change from baseline in the ITT population, for patients receiving anamorelin and placebo (PBO) in Romana 2. Data shown are observed values only (i.e., no modeling or imputation for missing data).

Key features of the Romana 2 study are as follows:
DESIGN: randomized, double-blind, placebo-controlled, multicenter, phase 3 study to evaluate the safety and efficacy of anamorelin HCl (anamorelin) in patients with NSCLC-Cachexia (59 sites; 15 countries)
PRIMARY ENDPOINT: Lean body mass (LBM) by DXA
SECONDARY ENDPOINTS:
　Key: pooled overall survival, Anorexia/Cachexia subdomain, Fatigue sub-domain, Simplified Evaluation of Appetite (SEA), and Simplified Evaluation of Fatigue (SEF)
　Other: Body weight, study specific overall survival, FAACT/FACIT-F trial outcome index (TOI) and total scores, additional LBM analyses
EXPLORATORY ENDPOINTS: Hunger Assessment Scale (HAS), Karnofsky (KPS), responder analyses; Population pharmacokinetics (PK) in 90 patients
STUDY POPULATION: advanced NSCLC (unresectable Stage III or IV) and cachexia (>5% body weight within 6 months or screening BMI<20 kg/m$^2$)
SAMPLE SIZE: 495 patients; randomization ratio 2:1 (anamorelin:placebo)
DOSING: placebo or 100 mg anamorelin for 12 weeks
SAFETY ASSESSMENTS: Adverse events (AEs), labs, vitals, ECGs FIG. 7 is a graphical representations of the results of a primary efficacy study (lean body mass), particularly the median change from baseline in the ITT population with regard to these endpoints. The figure depicts changes in LBM in patients receiving placebo (PBO) vs. anamorelin over the 12-week study period. Patients receiving anamorelin showed higher increases in LBM relative to patients receiving placebo. These results are also represented in Table 5 below.

TABLE 5

Analysis of Change from Baseline Over 12 Weeks in Lean Body Mass-ITT Population.

| | Lean Body Mass | |
|---|---|---|
| | Placebo (N = 165) | 100 mg anamorelin (N = 330) |
| N* | 157 | 321 |
| Median | −0.96 | 0.75 |
| 95% CI | −1.27, −0.46 | 0.51, 1.00 |
| Treatment Difference (anamorelin vs. placebo) | | |
| Median | 1.71 | |
| P-value** | <0.0001 | |

*Sample size takes into account those who were excluded due to missing baseline values and/or missing death dates.
**P-value is obtained from Wilcoxon Rank-sum test, taking into account missing post-baseline values (i.e., imputation), whereby lower ranks represent worse outcomes. The ranking order is determined by the average change from baseline in LBM at Week 6 and Week 12 with imputed values, and also by the survival date.

As shown in FIG. 7 and Table 5 above, anamorelin patients showed a highly statistically significant improvement in lean body mass (LBM). This was true for all subgroups except those patients with a BMI<18.5 (which may be due to a very small sample size of this subgroup).

Key secondary endpoints were measured in the MITT population, with a brief summary of results as follows. These results are further detailed in the following Figures and Tables.

In terms of health-related quality of life measurements (HR-QoL), results from the anorexia/cachexia domain of the FAACT assessment showed anamorelin provides statistically significant and clinically meaningful improvements in patient concerns related to these issues. Patients in the anamorelin group also had statistically significant and clinically meaningful improvements in regard to the SEA assessment, which focuses on feelings of early satiety, appetite, food consumption, and pressure by others to eat. HR-QoL assessments related to fatigue, listlessness and weakness, as measured by the Fatigue domain of FACIT-F, showed trends of improvement in specific subgroups who received anamorelin treatment, such as those aged 65 years and younger, patients with concomitant opioid use, patients with an ECOG of 2, and patients with a BMI<18.5. Patients in some subgroups, specifically patients with concomitant opioid use and patients with a BMI≤18.5, also had trends of improvement in regard to the SEF assessment, which focuses on feelings of fatigue and general weakness.

Figure 8A:
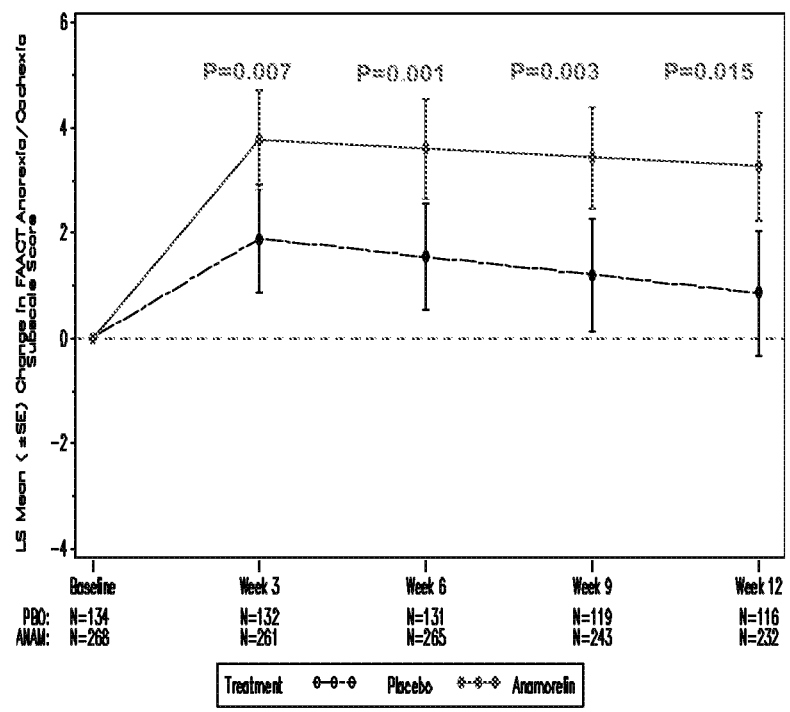
FIGS. 8A-B are graphical representations of patient symptoms and concerns related to cachexia as measured by change in FAACT anorexia/cachexia subscore and SEA score, specifically the treatment comparison of change from baseline at each visit in the MITT population in patients receiving anamorelin and placebo in Romana 2. Data shown are from a mixed-effects pattern-mixture model.
Figure 8B:
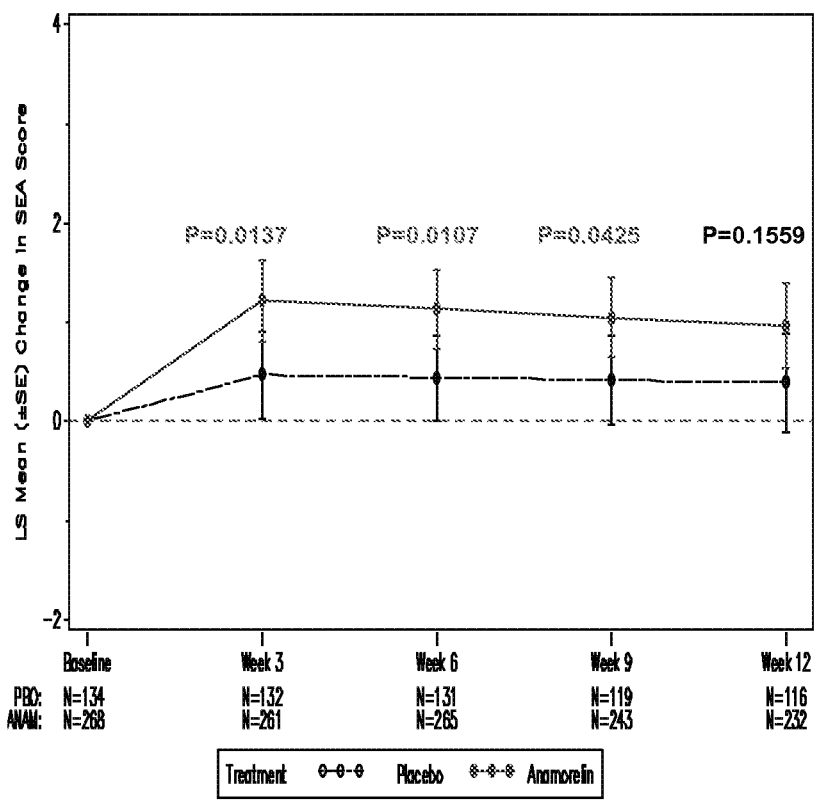

FIGS. 8A-B are graphical representations of patient symptoms and concerns related to cachexia as measured by FAACT anorexia/cachexia subscore and SEA score, specifically the treatment comparison of change from baseline at each visit in the MITT population, including the statistical significance of any differences in results from patients treated with placebo vs. anamorelin (p-values). Panel A shows the results for the anorexia/cachexia domain of FAACT in the MITT population over the 12-week study period, including the statistical significance of any differences in results from patients treated with placebo vs. anamorelin (p values). Patients in the anamorelin group showed statistically significant and clinically meaningful improvements in QoL related to concerns over cachexia. Panel B shows the results for the SEA score of FAACT in the MITT population over the 12-week study period, including the statistical significance of any differences in results from patients treated with placebo vs. anamorelin (p values). Patients in the anamorelin group showed statistically significant and clinically meaningful improvements in QoL concerns measured by the SEA, such as improvements in general appetite and consuming sufficient amounts of food, and decreases in early satiety and pressure by others to eat. Results are also presented below in Table 6. Data shown are from a mixed-effects pattern-mixture model.

TABLE 6

Analysis of Change from Baseline in HR-QoL Scores Over 12 Weeks-MITT Population.

| | Anorexia/Cachexia Domain | | SEA Score | |
|---|---|---|---|---|
| | Placebo (N = 136) | 100 mg anamorelin (N = 268) | Placebo (N = 136) | 100 mg anamorelin (N = 268) |
| N | 133 | 266 | 133 | 266 |
| LS Mean (SE) | 1.34 (1.032) | 3.48 (0.944) | 0.41 (0.435) | 1.08 (0.400) |
| Treatment Difference (anamorelin vs. placebo) | | | | |
| LS Mean (SE) | 2.14 (0.676) | | 0.66 (0.283) | |
| 95% CI | (0.81, 3.47) | | (0.11, 1.22) | |
| P-value | 0.0016 | | 0.0192 | |

*Note
that the minimally important difference (MID) is ~3 points for anorexia/cachexia domain and ~1 point for SEA score, and both were met with anamorelin treatment for each.

Figure 9A:
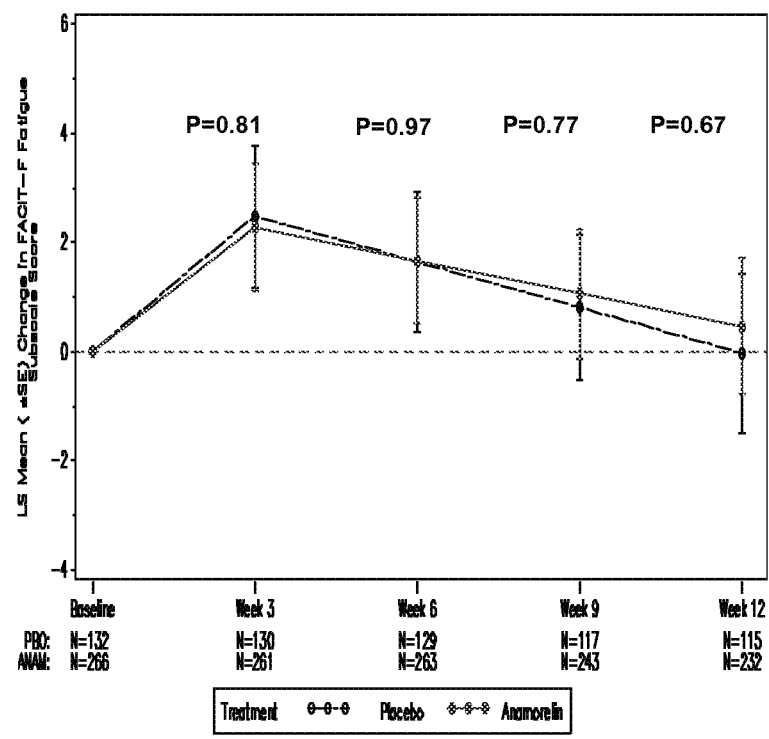
FIGS. 9A-B are graphical representations of patient symptoms and concerns related to fatigue as measured by change in FACIT-F fatigue subscore and SEF score, specifically the treatment comparison of change from baseline at each visit in the MITT population in patients receiving anamorelin and placebo in Romana 2. Data shown are from a mixed-effects pattern-mixture model.
Figure 9B:
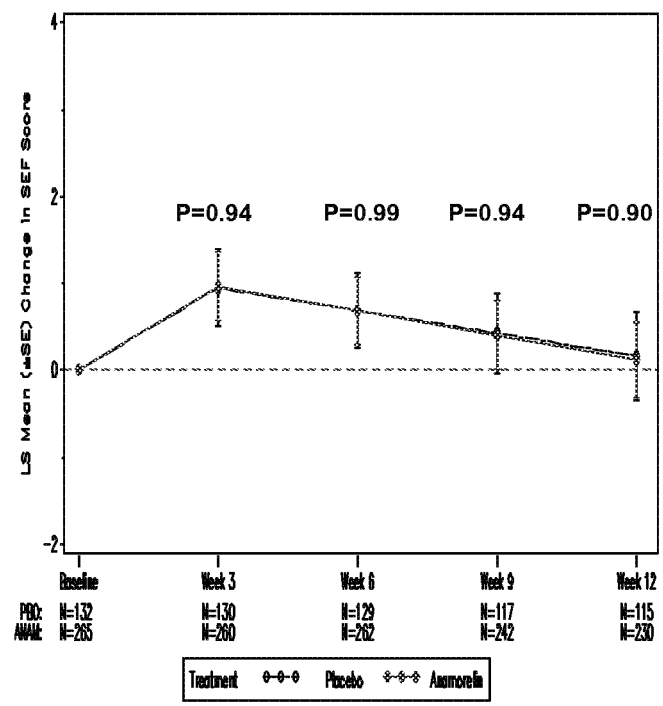
Figure 10A:
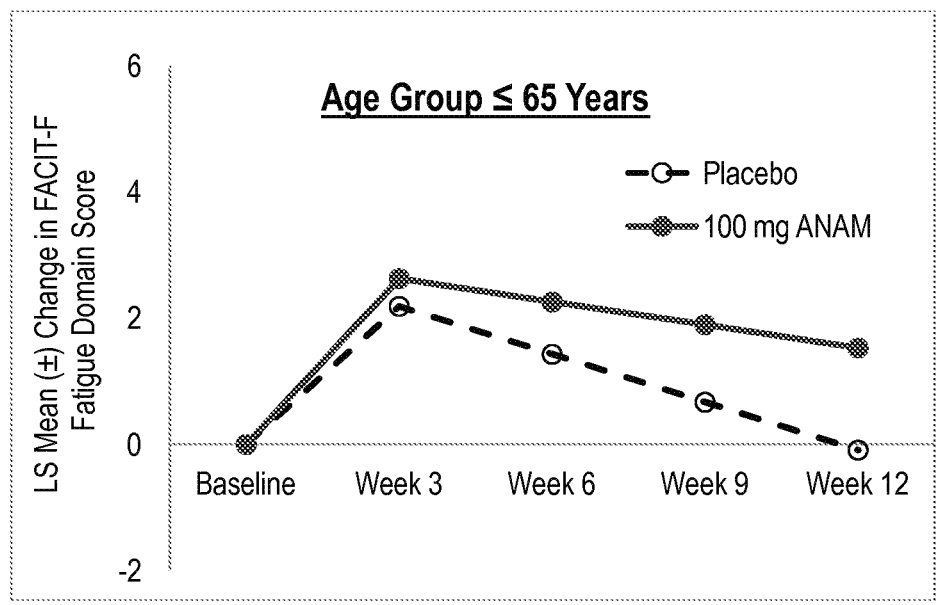
FIGS. 10A-D are graphical representations of the results for the Fatigue Domain of FACIT-F assessment over the 12-week study period in specific subgroups of MITT patients in Romana 2. Data shown are from a mixed-effects pattern-mixture model.
Figure 10B:
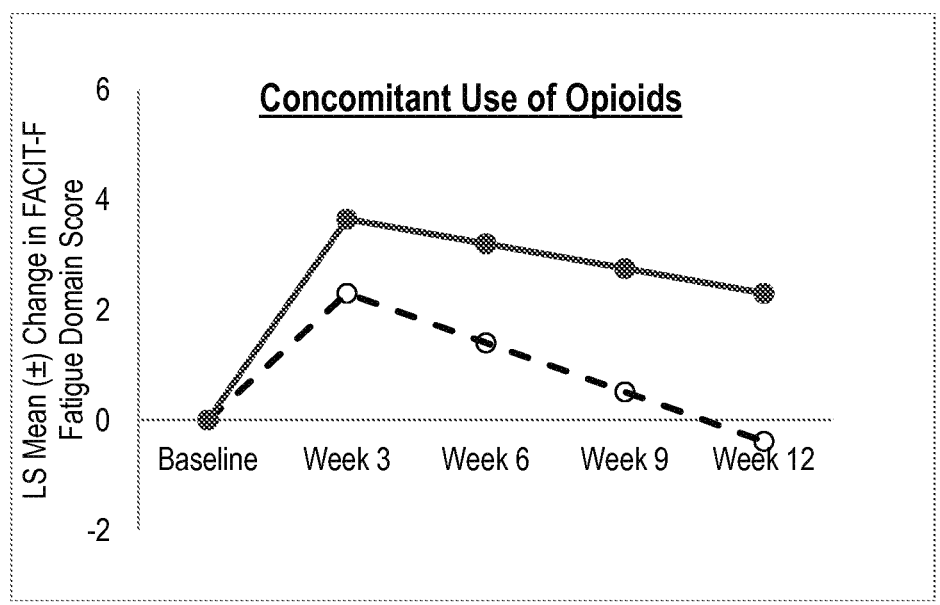
Figure 10C:
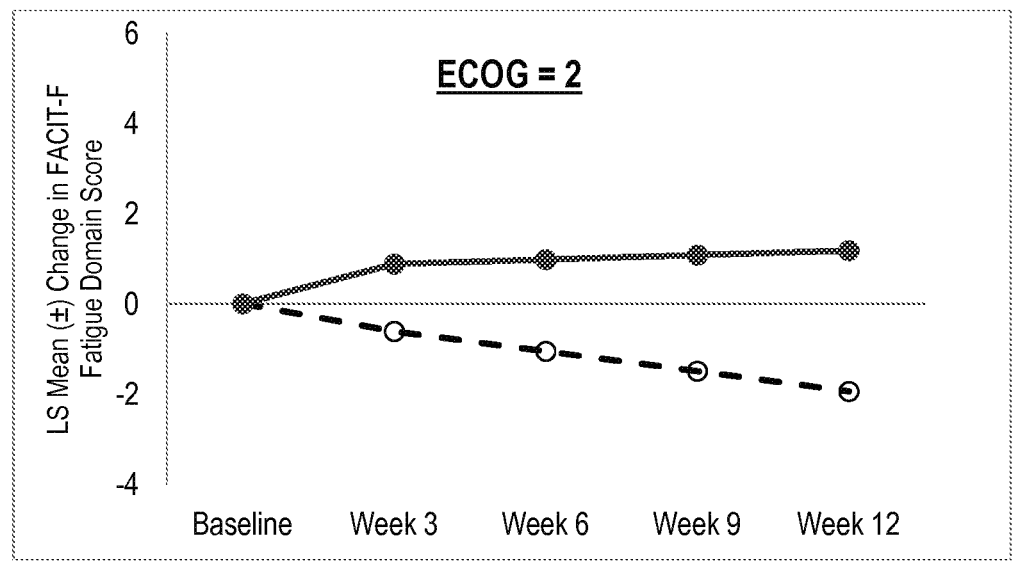
Figure 10D:
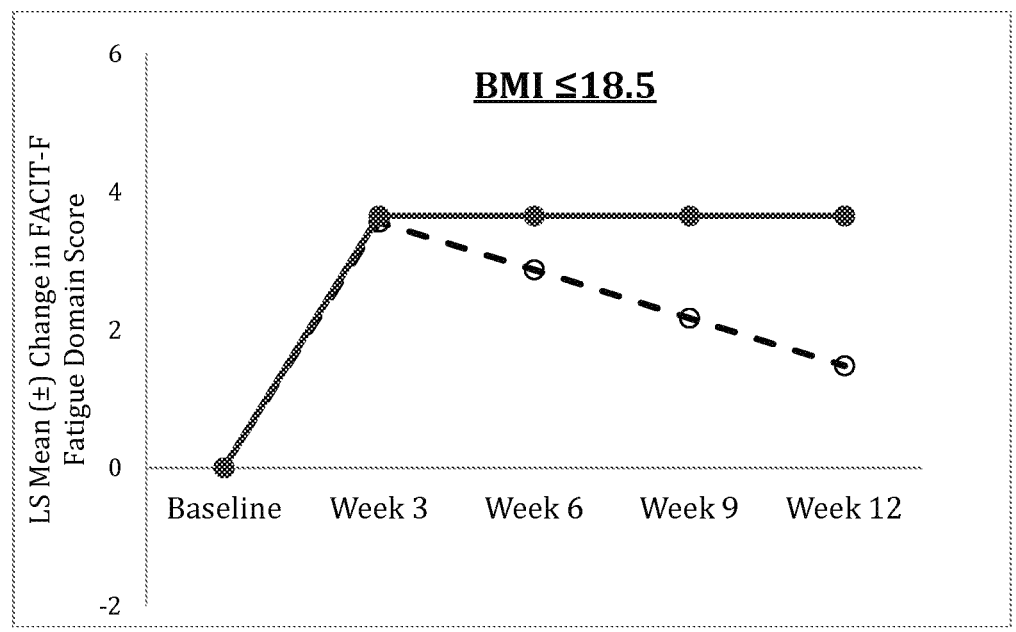

FIGS. 9A-B are graphical representations of patient symptoms and concerns related to fatigue as measured by FACIT-F fatigue subscore and SEF score, specifically the treatment comparison of change from baseline at each visit in the MITT population, including the statistical significance of any differences in results from patients treated with placebo vs. anamorelin (p-values). Panel A represents the results for the Fatigue Domain of FACIT-F assessment over the 12-week study period in MITT patients, including the statistical significance of any differences in results from patients treated with placebo vs. anamorelin. As can be seen in this panel, statistically significant improvements in the assessment were present in anamorelin patients versus those on placebo. Subgroups of interest receiving anamorelin showed trends of improvement in their fatigue levels; further details on these subgroups appear below and in FIGS. 10A-D (further described below). Panel B represents the results for the SEF score of FACIT-F assessment over the 12-week study period in MITT patients, including the statistical significance of any differences in results from patients treated with placebo vs. anamorelin. Here, there was an overall small trend of improvement among anamorelin patients in terms of lower fatigue, lower overall feelings of weakness, and lower amounts of time spent in bed; subgroups showed these trends of improvement as well. Specific improvements were noted in subgroups of patients with concomitant opioid use and patients with a BMI≤18.5. Data shown in FIGS. 10A-D are from a mixed-effects pattern-mixture model.

FIGS. 10A-D are graphical representations of the results for the Fatigue Domain of FACIT-F assessment over the 12-week study period in specific subgroups of MITT patients. Each of these subgroups showed improvement in the assessment among anamorelin patients relative to those patients in the placebo group. Panel A shows the improvement in FACIT-F fatigue score over the study period in patients under the age of 65; while there was some decrease in the fatigue score after Week 3, those patients in the treatment subgroup did not experience as severe of a decline in score as those in the placebo group, indicating improved fatigue assessment (i.e., less fatigue and/or weakness) due to the anamorelin treatment. Panel B shows the results of the FACIT-F fatigue score in patients who were concomitantly taking opioids; again, while there was some decrease in the score after Week 3, patients taking anamorelin did not experience as severe of a decline in score as those in the placebo group, again indicating that anamorelin treatment results in improved fatigue assessment (i.e., less fatigue and/or weakness) in this subgroup. Panel C represents score results from patients with an ECOG of 2. In this subgroup, anamorelin treatment provided a general trend of improvement in the FACIT-F score, indicating that these patients had less fatigue and/or weakness relative to those in the placebo group. Panel D shows the FACIT-F fatigue score in patients with a BMI less than or equal to 18.5. Patients in this subgroup who were in the anamorelin group maintained a steady score after Week 3, while those in the placebo group had a steady decline in score over these weeks, suggesting that patients in the anamorelin group had less fatigue and/or weakness relative to those in the placebo group.

Figure 11:
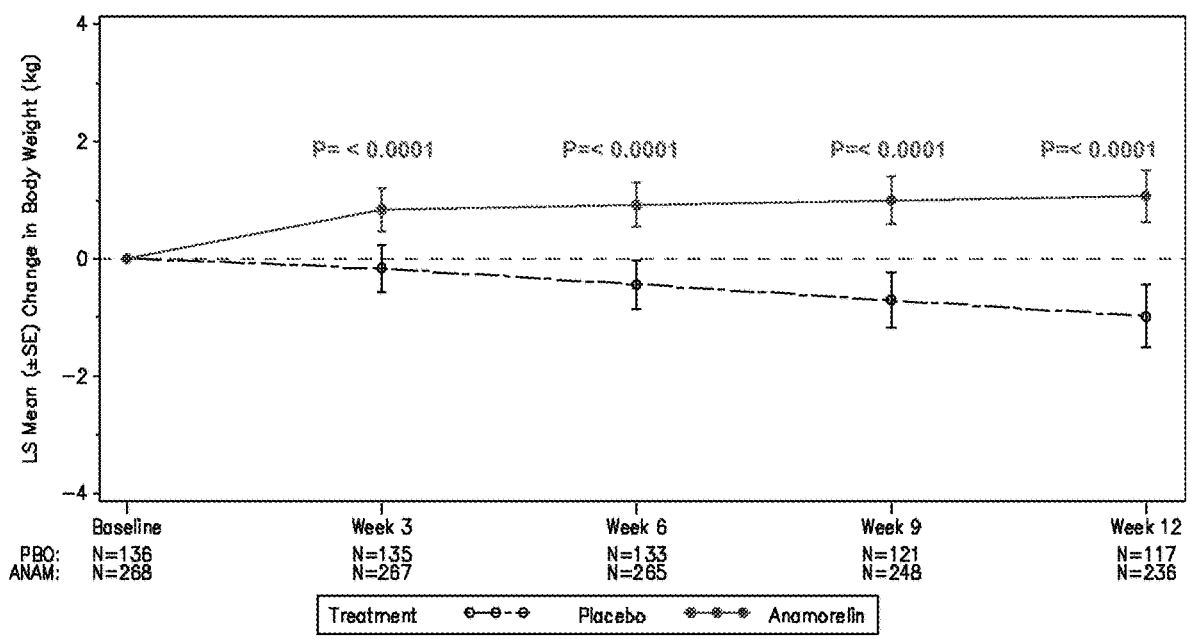
FIG. 11 is a graphical representation of the change from baseline in body weight of the MITT population over the course of the study, along with the statistical significance of the change (p-values).
Figure 12A:
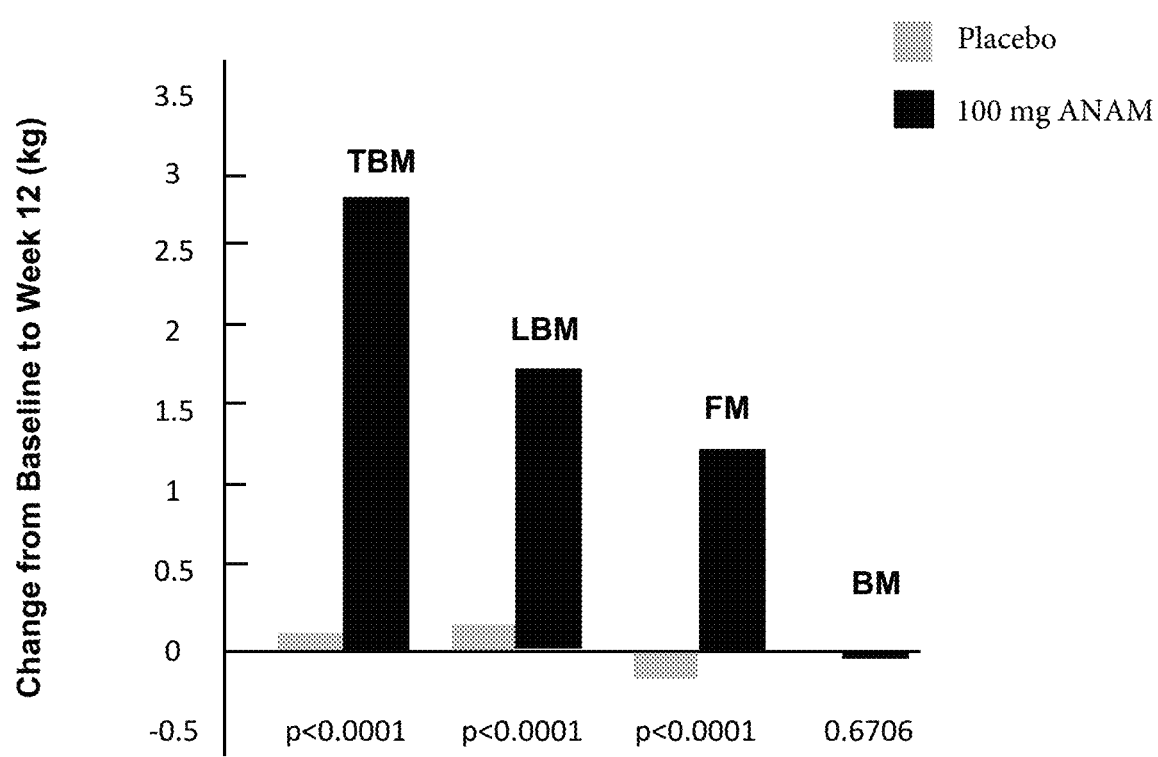
FIGS. 12A-B are bar graphs depicting the effect of administering 100 mg anamorelin daily for 12 consecutive weeks versus placebo in two separate blinded placebo controlled trials on total body mass, lean body mass, fat mass and bone mass in cancer patients (median change from baseline), in Romana 1 (12A) and Romana 2 (12B).
Figure 12B:
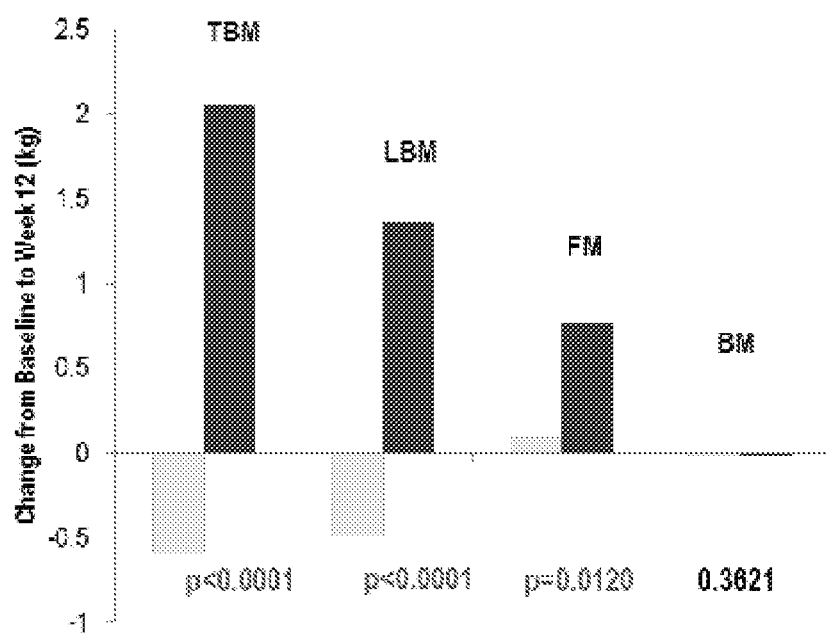

Key secondary endpoints in the MITT population, along with a brief statement of results of the endpoints, are summarized below. FIG. 11 and Table 9 below provide further data on body weight changes in this population.

Statistically significant and clinically meaningful improvements in body weight were seen in anamorelin patients relative to those taking placebo in the MITT population. In addition, a consistent improvement in LBM of anamorelin patients was seen. Finally, patients in the anamorelin group showed a trending benefit in cachexia concerns according to changes in the FAACT TOI and total score. No benefit of anamorelin was seen in FACIT-F TOI and total score.

FIG. 11 is a graphical representation of the change from baseline in body weight of the MITT population over the course of the study, including the statistical significance of any differences in results from patients treated with placebo vs. anamorelin (p-values). Patients in the anamorelin group experienced a statistically significant increase in body weight over the 12-week study, with the majority of the weight gain occurring by Week 3. Weight gain was maintained in the anamorelin group. The patients in the placebo group had a general decreasing trend of weight gain.

TABLE 7

Analysis of Change in Body Weight Over 12 Weeks-MITT Population.

| Overall Change from Baseline | Placebo (N = 136) | 100 mg anamorelin (N = 268) |
|---|---|---|
| N | 135 | 267 |
| LS Mean (SE) | −0.57 (0.438) | 0.95 (0.386) |
| Treatment Difference (anamorelin vs. placebo) | | |
| LS Mean (SE) | | 1.53 (0.327) |
| 95% CI | | (0.89, 2.17) |
| P-value | | <0.0001 |

*Note:
body weight may continue to increase with continued treatment past 12 weeks (i.e., observed mean values for change from baseline to Week 3, 6, 9, and 12 for anamorelin was 1.11 kg, 1.37 kg, 1.76 kg, and 1.91 kg, respectively).

Overall, the Romana 2 study found that the primary efficacy endpoint of LBM showed a statistically significant increase (p<0.0001) in patients in the anamorelin group relative to patients receiving placebo.

Health-related quality of life assessments showed that anamorelin treatment resulted in improved quality of life. The FAACT assessment anorexia/cachexia domain and Simplified Evaluation of Appetite (SEA) scores, which measured changes in appetite, early satiety, and food consumption, were significantly increased and exceeded minimally important difference thresholds, while FAACT TOI and total scores showed trending benefits for patients receiving anamorelin versus those in the placebo group. Moreover, patients in the anamorelin treatment group demonstrated anorexia-cachexia-related improvements (based on FAACT assessment) and enhanced appetites (based on SEA assessment) that were statistically significant and medically meaningful. The FACIT-F assessment fatigue domain and Simplified Evaluation of Fatigue (SEF), TOI and total scores were not statistically different from placebo, but general trends of improvement in some subgroups with anamorelin treatment were noted. Specifically, improvements in fatigue were seen in patients aged 65 years and younger, patients with concomitant opioid use, patients with ECOG of 2, and patients with a BMI≤18.5.

Consistent with absolute changes from baseline in LBM described above, measures of the percentage of change in LBM also shows consistent increases in anamorelin patients and decreases in placebo patients.

Figure 13A:
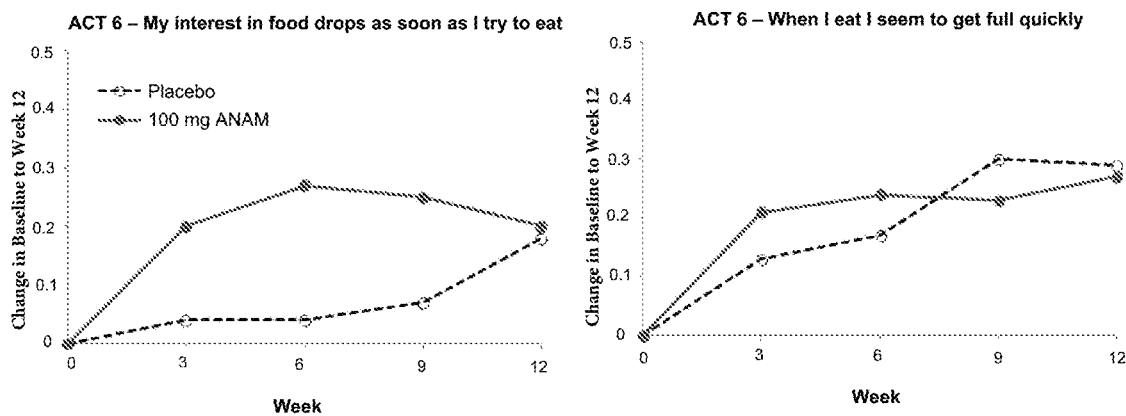
FIGS. 13A and 13B show the change from baseline over time in individual questions from the FAACT, early satiety, in Romana 1 and 2, respectively.
Figure 13B:
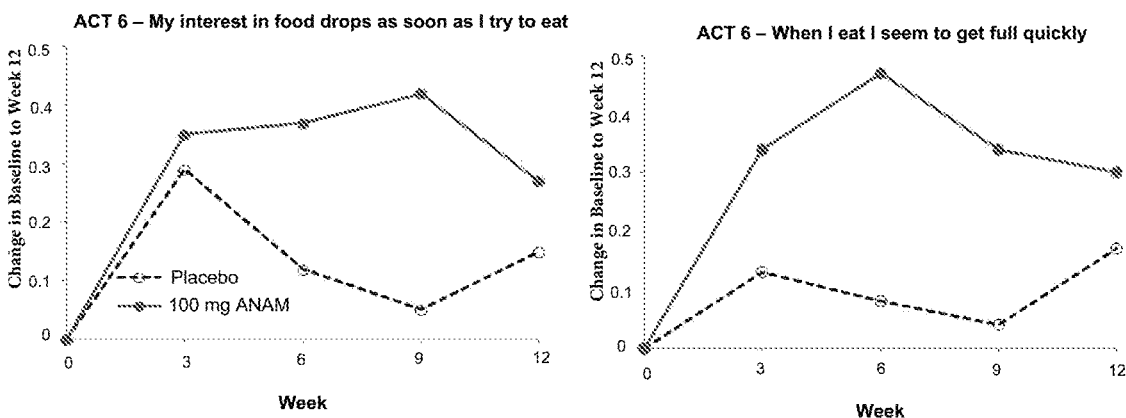

FIGS. 13a and 13b show the change from baseline over time in individual questions from the FAACT, early satiety, in Romana 1 and 2, respectively. Symptoms of early satiety and appetite showed an improvement in the anamorelin arm in Romana 2. Romana 2 also demonstrated an improvement in concerns related to weight and body image.

Overall, the Romana 2 study shows that anamorelin treatment for 12 weeks was well tolerated, and that the anamorelin therapy increased LBM and body weight while reducing CACS symptoms/concerns in advanced NSCLC patients with cachexia. These increases were highly statistically significant, and appeared to continue to increase with longer exposure. Some subgroups experienced improvements in fatigue assessments.

Throughout this application, various publications are referenced, The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of treating weight loss associated with cancer in a patient in need thereof comprising administering to said patient a therapeutically effective amount of anamorelin or a pharmaceutically acceptable salt thereof, wherein:
   a) said patient has a body mass index of <20 kg/m$^2$; and
   b) said patient has involuntary weight loss of >2% during the previous 6 months; and
   said method increases the body weight of said patient.

2. The method of claim 1, wherein said patient has an ECOG score of 0, 1, or 2.

3. The method of claim 1, further for treating low quality of life as measured by FAACT in the anorexia/cachexia domain in said patient, wherein said patient has low quality of life as measured by FAACT in the anorexia/cachexia domain and said method improves said low quality of life.

4. The method of claim 1, further for treating low quality of life as measured by FAACT in the anorexia/cachexia domain and low physical and functional well-being as measured by FAACT in the anorexia/cachexia domain in said patient, wherein:
   a) said patient has low quality of life as measured by FAACT in the anorexia/cachexia domain; and
   b) said patient has low physical and functional well-being as measured by FAACT in the anorexia/cachexia domain; and
   said method improves said low quality of life and said low physical and functional well-being.

5. The method of claim 1, wherein said patient has stage III unresectable or stage IV NSCLC.

6. The method of claim 1, wherein said therapeutically effective amount comprises 100 mg of anamorelin or a pharmaceutically acceptable salt thereof once daily.

7. The method of claim 1, wherein said therapeutically effective amount comprises 100 mg of anamorelin HCl based on the weight of the salt administered once daily.

8. The method of claim 4, wherein said therapeutically effective amount comprises 100 mg of anamorelin or a pharmaceutically acceptable salt thereof once daily.

9. A method of treating weight loss associated with cancer, and anorexia symptoms as measured by FAACT in the anorexia/cachexia domain, in a patient in need thereof comprising administering to said patient a therapeutically effective amount of anamorelin or a pharmaceutically acceptable salt thereof, wherein:
- a) said patient has a body mass index of <20 kg/m$^2$;
- b) said patient has involuntary weight loss of >2% during the previous 6 months;
- c) said method increases the body weight of said patient; and
- d) said method improves said anorexia symptoms.

10. The method of claim 9, wherein said patient has an ECOG score of 0, 1, or 2.

11. The method of claim 9, further wherein said patient has low quality of life as measured by FAACT in the anorexia/cachexia domain and said method improves said quality of life.

12. The method of claim 9, wherein said patient has stage III unresectable or stage IV NSCLC.

13. The method of claim 9, wherein said therapeutically effective amount comprises 100 mg of anamorelin or a pharmaceutically acceptable salt thereof once daily.

14. The method of claim 9, wherein said therapeutically effective amount comprises 100 mg of anamorelin HCl based on the weight of the salt administered once daily.

15. The method of claim 9, wherein said patient has low physical and functional well-being as measured by FAACT in the anorexia/cachexia domain and said method improves said physical and functional well-being.

16. The method of claim 9, wherein said improvement in anorexia symptoms is measured by a subset of FAACT in the anorexia/cachexia domain.

17. The method of claim 9, wherein said improvement in anorexia symptoms is measured by the entire FAACT in the anorexia/cachexia domain.

* * * * *